(12) United States Patent
Hirakuni et al.

(10) Patent No.: US 6,328,866 B1
(45) Date of Patent: Dec. 11, 2001

(54) ION SENSOR AND ION SENSOR PLATE

(75) Inventors: Shoichiro Hirakuni; Keiichi Ida; Masatsugu Suzuki; Akihiko Mochizuki, all of Tokyo (JP)

(73) Assignee: Taiyo Yuden Co., Ltd., Tokyo (JP)

(*) Notice: Subject to any disclaimer, the term of this patent is extended or adjusted under 35 U.S.C. 154(b) by 0 days.

(21) Appl. No.: 09/220,789

(22) Filed: Dec. 28, 1998

(30) Foreign Application Priority Data

Dec. 29, 1997 (JP) .................................................. 9-367808

(51) Int. Cl.$^7$ .................................................. G01N 27/333
(52) U.S. Cl. ........................ 204/416; 204/418; 204/435
(58) Field of Search .................................. 204/416, 418, 204/419, 435

(56) References Cited

U.S. PATENT DOCUMENTS

| | | | |
|---|---|---|---|
| 2,672,441 | * 3/1954 | White | 204/419 |
| 3,563,874 | * 2/1971 | Ross et al. | 204/419 |
| 3,686,091 | 8/1972 | Sawa et al. | |
| 4,053,381 | * 10/1977 | Hamblen et al. | 204/418 |
| 4,361,473 | * 11/1982 | Young et al. | 204/418 |
| 4,505,801 | 3/1985 | Detwiler et al. | |
| 4,773,969 | * 9/1988 | Miura et al. | 204/418 |
| 5,021,140 | 6/1991 | Sato . | |
| 5,505,836 | * 4/1996 | Miyahara et al. | 204/418 |
| 5,897,758 | * 4/1999 | Musacchio et al. | 204/418 |
| 5,911,862 | * 6/1999 | Chan | 204/418 |

FOREIGN PATENT DOCUMENTS

| | | |
|---|---|---|
| 34 38 221 A1 | 10/1994 | (DE) . |
| 170375 | 2/1986 | (EP) . |
| 394990 | 10/1990 | (EP) . |
| 0498572 | 8/1992 | (EP) . |
| 60-168050 | 8/1985 | (JP) . |
| 3-002554 | 1/1991 | (JP) . |
| 302554 | 1/1991 | (JP) . |
| 3-087644 | 4/1991 | (JP) . |
| 387644 | 4/1991 | (JP) . |

OTHER PUBLICATIONS

A. Marton et al., "The Standard Potential of Heterogeneous Precipitate–based Membrane Electrodes"Anal. Chim. Acta, 54 (1971) 209–219.

Dong Liu et al., "Enhancing EMF Stability of Solid–state Ion–selective Sensors by Incorporating Lipophilic Silver–ligand Complexes Within Polymeric Films"Analytica Chimica Acta 321 (1996) 173–183.

B. P. Nikolskii et al., "Solid Contact In Membrane Ion–selective Electrodes"Ion–selective Electrode Rev., 1985, vol. 7, pp. 3–39.

G.I. Shumilova et al., "Solid–contact Sodium–selective Electrode B ased on a Neutral Complexing Agent"Sov Electrochem, May 1984, vol 20, No. 5, pp. 667–668.

Peter L. Bailey, "Analysis with Ion–selective Electrodes"1980, Heyden & Son, Ltd., London, p.18, line 19 –p. 20, line2.

* cited by examiner

Primary Examiner—T. Tung
(74) Attorney, Agent, or Firm—Birch, Stewart, Kolasch & Birch, LLP

(57) ABSTRACT

An ion sensor and an ion sensor plate provided with an ion sensitive membrane which is characterized in that the ion sensitive membrane contains a material constituting the dissociation equilibrium of Ag/X, and an excessive quantity of an ion sensitive material or an anion scavenger. A coated film of surfactant is provided at the inner face of the passageway communicating with the test liquid-measuring electrode so as to add the surfactant to the test liquid. The plasticizer is added at a ratio of 65 to 80% by weight. The atomic ratio of silver and halogen in the silver halide layer is set to at least 1.2. The particle diameter of the modified silver halide layer is set to at most 1 $\mu$m.

18 Claims, 8 Drawing Sheets

ION SENSOR AND ION SENSOR PLATE

BACKGROUND OF THE INVENTION

This invention relates to an ion sensor for various kinds of ion that can be employed in the examination of blood, etc. This invention also relates to a disposable simplified ion sensor plate partially constituting the ion sensor.

The ion sensor is generally formed of a structure comprising a silver/silver halide (Ag/AgX) electrode wherein a silver halide layer is deposited on a silver layer, an inner electrolyte solution, and an ion sensitive membrane (ISM). Since an inner electrolyte solution is employed in the ion sensor as described above, a vessel for accommodating the inner electrolyte solution is required. As a result, it has been very difficult to miniaturize the ion sensor or to make the ion sensor into a disposable type.

Under the circumstances, there has been developed a disposable simplified ion sensor plate for examining a blood sample, etc., and some kinds of it have been actually proposed.

As one example of such proposals, there has been known a differential type multi-ion sensor wherein a multi-ion sensor plate is connected with a measuring circuit thereby to measure concurrently the concentrations of many different kinds of ion. This multi-ion sensor is constructed as shown in FIG. 2. Namely, it comprises a multi-ion sensor plate main body 5 provided with 5 groups of electrode pairs, each group consisting of a test liquid-measuring electrode 2a and a reference electrode 2b, which are formed on a glass-epoxy resin substrate 1 by a process wherein copper electrodes are formed in advance by means of an etching process and then subjected to an electrolytic silver plating thereby to form a silver layer thereon, and with silver chloride layers 4a and 4b deposited on the silver layer formed on one end portion of each test liquid-measuring electrode 2a as well as on the silver layer formed on one end portion of each reference electrode 2b which faces the aforementioned one end portion of the test liquid-measuring electrode 2a, the other end portions of these electrodes 2a and 2b which are remote from the aforementioned one end portions being constituted as an outer electrode, respectively.

The multi-ion sensor further comprises a channel body 9 which is designed to be contactingly superimposed on the multi-ion sensor plate main body 5 and consists of a polyester film provided with through-holes 6a to 6e and 6'a to 6'e communicating with the silver chloride layers 4a and 4b of each group of an electrode pair, respectively, with an elongated hole constituting a liquid junction portion 7 which is formed to coincide with the forward ends of two channels of the upper cell to be explained hereinafter and is designed to allow a test liquid to be contacted with the reference liquid, and with through-holes 8a and 8b communicating respectively with the electrodes 2a and 2b of each group of an electrode pair.

Various kinds of ion-sensitive film-forming solution containing various kinds of ion-sensitive material such as a large cyclic compound called ionophore or an ion-exchange resin are individually applied through these through-holes 6a to 6e and 6'a to 6'e to the surfaces of silver chloride layers 4a and 4b, and then dried to form five kinds of different ion-sensitive films on the surfaces of silver chloride layers 4a and 4b.

The combined body consisting of this multi-ion sensor plate main body 5 and channel body 9 is then fitted in the recessed portions 10a and 10b of a lower cell 10 formed of a transparent acrylic resin plate. The resultant lower cell 10 is subsequently superimposed thereon with an upper cell 12 formed of a transparent acrylic resin via a pressure sensitive adhesive double coated tape so as to bond the lower cell 10 and the upper cell 12 to each other, thus packaging the aforementioned combined body.

The upper cell 12 is provided on the reverse surface thereof with a couple of channels 13 and 14 which are partitioned by a barrier wall and communicated with the through-holes 6a to 6e and 6'a to 6'e, respectively, each channel being formed of a U-shaped groove. A test liquid inlet portion 15 and a reference liquid inlet portion 16 are formed to communicate respectively with one end of the channels 13 and 14. A pair of air vent grooves 13a and 14a each being formed of a U-shaped groove of small width and bent into an L-shape are symmetrically disposed to communicate with the other end of the channels 13 and 14, respectively. The distal ends of these air vent grooves 13a and 14a are communicated with vertical passageways 13b and 14b formed at the forward end portions of the test liquid inlet portion 15 and the reference liquid inlet portion 16, respectively.

The upper cell 12 is further provided with terminal-insertion holes 18a and 18b for allowing the terminals of the measuring apparatus (not shown) to be inserted therein, the location of these terminal-insertion holes 18a and 18b coinciding with the exposed terminals of the outer electrodes of the test liquid-measuring electrode 2a and the reference electrode 2b.

When this multi-ion sensor plate is to be employed, a test liquid and a reference liquid are introduced by making use of a syringe, etc. into the test liquid inlet portion 15 and the reference liquid inlet portion 16, respectively. As a result, these liquids are supplied through the channels 13 and 14 to the ion-selective electrodes in the through-holes 6a to 6e and 6'a to 6'e, respectively, and at the same time, the test liquid is contacted with the reference liquid at the liquid junction portion 7. Under this condition, the terminals of measuring apparatus are inserted into the terminal-insertion holes 18a and 18b so as to be contacted with the outer electrodes respectively, thereby measuring the ionic components of the test liquid. As a result, the concentrations of 5 kinds of ion can be measured simultaneously with a single injection of these test liquid and reference liquid.

Even in the case where an ion-sensitive film is directly formed on the surface of Ag/AgX electrode as described above, the electric potential to be generated can be determined by the dissociation equilibrium represented by the formula: $AgX \leftrightharpoons Ag^+ + X^-$ as in the case of an the ordinary ion sensor. However, when a composition comprising polyvinyl chloride type resin and a plasticizer thereof is employed as an ion-sensitive film, the AgX constituting the underlying layer is dissolved mainly by the solubilizing power of this plasticizer, i.e. this ion-sensitive film is capable of functioning in the same manner as that of the inner electrolytic solution employed in the ordinary ion sensor.

In this case, the dissolving degree of the AgX layer can be controlled in a certain degree by the grain size and surface roughness of the AgX layer, and the electric potential to be generated can be controlled within a relatively limited range as made clear in our previous patent applications (Japanese Patent Applications H/1-135728 and H/1-222909).

By the way, in the structure where an ion sensitive membrane is directly formed on the surface of silver chloride layer without providing an inner aqueous electrolyte solution layer as mentioned above, the ion sensitive layer is formed by a process wherein a solution of a mixture containing a sensitive material or so-called ionophore which is selectively sensitive to an ion to be detected, and a salt such as an anion scavenger for eliminating the interference of anion originating from a test liquid or a reference liquid is prepared at first, and then coated on the surface of a matrix formed of polyvinyl chloride type resin for instance. However, in order to ensure the flexibility of this coated film so as to prevent the coated film from being peeled off from an underlying layer or from being cracked, a plasticizer is concurrently mixed into the ion sensitive membrane.

There is a possibility that plasticizer that has been incorporated into the ion sensitive membrane may be eluted into a test liquid or a reference liquid at the occasion of employing these liquids, or into a washing solution at the occasion of repeatedly using an ion sensor plate provided with this ion sensitive membrane. If the quantity of plasticizer thus eluted becomes large, the aforementioned ionophore and salt may also be eluted together with the elution of the plasticizer, thus deteriorating the property of the ion sensitive membrane. In view of this phenomenon, the mixing ratio of polyvinyl chloride type resin (the matrix of the ion sensitive membrane) and the plasticizer is generally confined to at most 35% by weight and 60–65% by weight, respectively based on the total weight of the ion sensitive membrane.

As mentioned above, since the dissolution degree of the AgX into the ion sensitive membrane changes not only due to a transient change in the dissolving process thereof into the ion sensitive membrane, but also due to changes in environmental conditions such as ambient temperature, ambient humidity, etc., if the AgX is left to dissolve spontaneously into the ion sensitive membrane, it is almost impossible to completely control these delicate changes in conditions even if it would have been possible to control the physical property of the AgX layer as described above. However, since there is a strong demand for a high precision ion sensor which is free from inconsistency of measured values, an ion sensor plate constituting an important component of the ion sensor is required to be subjected, after the manufacture thereof, to corrections in the initial characteristics thereof or to selection for picking up only those meeting the specification, as any discrepancy in measured values can be manifested as an error in generated potential of electrode in the inspection for quality control in the manufacturing site. Further, if any error in measurement is desired to be minimized, it is required to wait until an equilibrium state where the dissolution of AgX into the ion sensitive membrane can no more be proceeded any further is reached, thus inevitably raising the problem of cost increase in viewpoint of manufacturing steps.

The dissolution of AgX into the ion sensitive membrane can occur not only immediately after the manufacture of the ion sensor plate but also with the lapse of time. For example, even after 30 days, the electric potential at the interface between the AgX layer and the ion sensitive membrane may not be stabilized and the inconsitency of electric potential may become more conspicuous.

In the measurement of concentration of ions in blood, the effects of factors reflecting the quantity of hemocyte or protein in the blood, or so-called hematocrit (Hct) value (the volumetric ratio of erythrocyte in the blood) may be conceivable. However, no countermeasures have been taken as yet against this problem.

Properly speaking, it may be ideal to correct the measured value of ion concentration by taking this Hct value into consideration. However, since this Hct value varies depending on individual, i.e. the Hct value varies within the range of 42 to 45 in the case of adult men, and within the range of 38 to 42 in the case of adult women, and further, since there are various kinds of measuring methods, resulting in varied values depending on the method adopted, such a countermeasure has not been adopted because of poor reliability in measured values in general.

Under the circumstances, there is no other way but to adopt the values of ion concentration that can be obtained by making use of the aforementioned multi-ion sensor plate. However, there is a possibility of obtaining an abnormal value in ion concentration value depending on the hematocrit value (Hct %), i.e. depending on the quantity of hemocyte or protein in the blood. For example, when the Hct value is in the range of 40 to 50%, the value of Ca may become 0.1 to 0.2 mM (millimole/liter, the same hereinafter) lower or higher than the real value, and the value of Na may become about 2 to 5 mM lower or higher than the real value. In view of this problem, it is now desired to develop a method as well as an apparatus for measuring ion concentration which is free from the aforementioned undesirable effects.

In the method of forming an ion sensitive membrane by dripping a solution of raw material mixture in tetrahydrofran solvent onto an underlying layer, the surface or interior of the coated film is suffered from convection at the occasion of air drying after coating, thus turning the coated surface into the state of so-called orange peel and causing the coated film to lose its fluidity to be solidified as it is. As a result, it is impossible to assure the uniformity of the film.

Further, since polyvinyl chloride resin constituting the matrix cannot be sufficiently plasticized, it would become impossible to render the ion sensitive membrane to sufficiently wet to or spread over the underlying silver chloride layer, thus causing the contact surface thereof with the underlying layer to become insufficient.

Additionally, as being clarified in the invention recited in the appended claims, even if at least one kind of material for constituting the dissociation equilibrium of silver halide such as silver chloride or a material for dissociating the aforementioned at least one kind of material is added to the ion sensitive membrane in addition to the aforementioned components for the purpose of stabilizing the aforementioned dissociation equilibrium ($AgX \leftrightarrows Ag^+ + X^-$); or even if the same kind of ionophore as employed in the ion sensitive membrane is excessively added to the ion sensitive membrane; or even if an anion scavenger such as TPB (tetrakisphenyl borate) is excessively added to the ion sensitive membrane for the purpose of controlling the stability of the dissociation equilibrium of: $Ag-TPB = Ag^+ + TPB^-$ substantially substituting the aforementioned dissociation equilibrium of: $AgX \leftrightarrows Ag^+ + X^-$, it is impossible to expect a sufficient effect of stabilizing these dissociation equilibriums, i.e. the electric potential to be generated at the interface between the silver halide layer of the electrode and the ion sensitive membrane.

If the composition of the ion sensitive membrane becomes non-uniform, and the contacting area of the ion sensitive membrane with the underlying layer becomes insufficient, the measured values of ion concentration to be detected from a test liquid becomes inconsistent, thus failing to obtain a satisfactory measurement precision.

In particular, if the electric potential measured of electrode of the main ion sensor body or ion sensor plate immediately after the manufacture thereof is inconsistent, i.e. if the initial characteristic of them is inconsistent, it is impossible to obtain a high measurement precision. As a result, it is required to correct the initial characteristics thereof or to select only those meeting the specification, thus inevitably raising the cost increase in viewpoint of productivity.

In the case where an ion sensor film is formed on an Ag/AgX electrode such as a silver/silver chloride electrode, it is required to stabilize the dissociation equilibrium of: $AgX \leftrightarrows Ag^+ + X^-$ at the AgX layer. For the purpose of achieving this stabilization, a stabilizing agent may be incorporated into the ion sensitive membrane as suggested by this invention recited in the appended claims.

However, even when the resistance of the interface between the ion sensitive membrane and the AgX layer contacted with the ion sensitive membrane is high, the output of the multi-ion sensor is more likely to be influenced by the electric voltage to be generated by an electric resistance at the interface of electric current passing through a measuring circuit, and hence the precision of detected value obtained from the output, i.e. the measurement precision of ion concentration which is converted from the aforementioned detected value would be badly affected.

As measures for minimizing the electric resistance at the interface between the ion sensitive membrane and the AgX layer, the contacting area between the ion sensitive membrane and the AgX layer may be increased, or the electric resistance of the AgX layer may be minimized.

If the contacting area between the ion sensitive membrane and the AgX layer is desired to be increased, the particle diameter of the AgX may be reduced so as to increase the surface area of the AgX layer as is well known in the art. For example, Japanese Patent Publication H/7-214882 suggests to reduce the particle diameter of the AgX to 1 $\mu$m or less. When an ion sensitive membrane containing polyvinyl chloride-based resin and a plasticizer for this resin is to be employed, the content of the plasticizer in the ion sensitive membrane may be increased so as to form an ion sensitive membrane having a sufficient pliability to conform with the fine rugged surface of the AgX layer, thereby increasing the contact area of the ion sensitive membrane. The effectiveness of this method is clarified in the invention to be recited in the appended claims.

However, the effects to be obtained by the measures to minimize the particle diameter of AgX or to increase the contacting area of the ion sensitive membrane as mentioned above are limited due to the limited area of the electrode on which the ion sensitive membrane is to be mounted. It is desired, in addition to these measures, to incorporate a potential-stabilizing agent into the ion sensitive membrane and at the same time, to modify the AgX layer per se so as to minimize the electric resistance of the AgX layer.

BRIEF SUMMARY OF THE INVENTION

Accordingly, a first object of the present invention is to provide an ion sensor and an ion sensor plate, which are excellent in initial characteristics immediately after the manufacture thereof, minimal in inconsistency in characteristics, and capable of saving the time for carrying out the correction of the initial characteristics or the stabilization of the characteristics.

A second object of the present invention is to provide an ion sensor and an ion sensor plate, which are capable of exhibiting a high precision measuring value not only immediately after the manufacture thereof, but also after a lapse of time.

A third object of the present invention is to provide an ion sensor and an ion sensor plate, which are capable of maintaining the dispersion stability of submerged and dispersed substances such as hemocyte or protein reflecting the hematocrit in a test liquid to be supplied to the measuring electrode of the test liquid at the occasion of measurement so as to prevent the dispersed substances from being settled on the test liquid-measuring electrode at the occasion of measurement.

A fourth object of the present invention is to provide an ion sensor and an ion sensor plate, which are capable of not indicating an abnormal value in the measurement of ion concentration even if the dispersion state of the submerged and dispersed substances such as hemocyte or protein reflecting the hematocrit is changed.

A fifth object of the present invention is to provide an ion sensor and an ion sensor plate provided with an ion sensitive membrane having an uniform composition.

A sixth object of the present invention is to provide an ion sensor and an ion sensor plate provided with an ion sensitive membrane which makes it possible to increase the contacting area thereof with an underlying layer.

A seventh object of the present invention is to provide an ion sensor and an ion sensor plate, which enable the effect of a potential-stabilizing agent incorporated in the ion sensitive membrane to be effectively manifested.

An eighth object of the present invention is to provide a disposable simple-structured ion sensor and a disposable simple-structured ion sensor plate, which are capable of minimizing any bad influence even if a plasticizer, etc. is dissolved in a test liquid or a reference liquid.

A ninth object of the present invention is to provide an ion sensor and an ion sensor plate, which are provided with a silver/silver halide electrode which is capable of minimizing the electric resistance of a silver halide layer, and to provide a method of manufacturing these ion sensor and ion sensor plate.

A tenth object of the present invention is to provide an ion sensor and an ion sensor plate, which are capable of minimizing the electric resistance at the interface between the silver halide layer of a silver/silver halide electrode and an ion sensitive membrane, and to provide a method of manufacturing these ion sensor and ion sensor plate.

An eleventh object of the present invention is to provide an ion sensor and an ion sensor plate, which are capable of easily and readily increasing the atomic ratio of silver/halogen of a silver halide layer of a silver/silver halide electrode, and to provide a method of manufacturing these ion sensor and ion sensor plate.

A twelfth object of the present invention is to provide an ion sensor and an ion sensor plate, which are capable of increasing the atomic ratio of silver/halogen of a silver halide layer of a silver/silver halide electrode without leaving impurities in the silver halide layer while allowing the resistance of the silver halide layer as well as the non-uniformity in resistance thereof to be minimized, and to provide a method of manufacturing these ion sensor and ion sensor plate.

A thirteenth object of the present invention is to provide an ion sensor and an ion sensor plate, which enable the manipulation thereof to be easily performed, and are easy to use, simple in structure and are capable of saving the manufacturing cost, thus enhancing the productivity thereof.

In order to solve the aforementioned problems, this invention provides (1) an ion sensor comprising an ion sensor plate main body provided with at least one group of electrode pair, each group consisting of a test liquid-measuring electrode and a reference electrode, each provided with a silver halide layer formed on a silver layer and with an ion sensitive membrane which is sensitive to a specific ion and formed on said silver halide layer; and a measuring circuit connected with said ion sensor plate main body for measuring a concentration of said specific ion in said test liquid;

wherein said ion sensitive membrane contains an electric potential-stabilizing agent which is capable of stabilizing an electric potential at an interface between said silver halide layer and said ion sensitive membrane.

This invention also provides (2) an ion sensor as set forth in the aforementioned item (1) wherein said electric potential-stabilizing agent is composed of a halogen ion and/or silver ion, or a compound which is capable of dissociating a halogen ion and/or silver ion.

This invention also provides (3) an ion sensor as set forth in the aforementioned item (1) or (2) wherein said electric potential-stabilizing agent is silver halide.

This invention also provides (4) an ion sensor as set forth in any of the aforementioned item (1) to (3) wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an ion sensitive material which is higher than that is required for responding to said specific ion.

This invention also provides (5) an ion sensor as set forth in the aforementioned item (1) wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an electric potential-stabilizing agent which is higher than that is required for eliminating said disturbance by said anion.

This invention also provides (6) an ion sensor as set forth in the aforementioned item (1) or (2), which is further provided with a test liquid-feeding passageway for supplying said test liquid to said test liquid-measuring electrode and with a reference liquid-feeding passageway for supplying said reference liquid to said reference electrode, wherein at least said test liquid-feeding passageway among these passageways is provided with a coated film of surfactant which is capable of adding said surfactant to said test liquid as said test liquid passes through said test liquid-feeding passageway.

This invention also provides (7) an ion sensor as set forth in the aforementioned item (1) or (2) wherein said ion sensitive membrane contains at least a matrix, a plasticizer for plasticizing said matrix and an ion sensitive material, the content of said plasticizer being 65 to 80% by weight based on said ion sensitive membrane.

This invention also provides (8) an ion sensor as set forth in the aforementioned item (1) or (2) wherein said silver halide layer formed on said silver layer is a modified silver halide layer which is modified in such a manner that the atomic ratio of silver and halogen: Ag/Cl is at least 1.2.

This invention also provides (9) an ion sensor as set forth in the aforementioned item (8) wherein a particle diameter of said silver halide and of said silver in said modified silver halide layer is at most 1 $\mu$m.

This invention also provides (10) an ion sensor plate comprising an ion sensor plate main body having a substrate and provided on the substrate with at least one group of electrode pair, each group consisting of a test liquid-measuring electrode and a reference electrode, each provided with a silver halide layer formed on a silver layer and with an ion sensitive membrane formed on said silver halide layer; an upper cell which is designed to form a closed channel for supplying a test liquid to said test liquid-measuring electrode and a closed channel for supplying a reference liquid to said reference electrode, and is provided with a test liquid inlet portion communicating with said closed channel for supplying said test liquid and with a reference liquid inlet portion communicating with said closed channel for supplying said reference liquid; and a liquid junction portion which is formed in said ion sensor plate main body and designed to allow said test liquid and said reference liquid supplied through said channels respectively to be contacted with each other;

wherein said ion sensitive membrane contains an electric potential-stabilizing agent which is capable of stabilizing an electric potential at an interface between said silver halide layer and said ion sensitive membrane.

This invention also provides (11) an ion sensor plate as set forth in the aforementioned item (10) wherein said electric potential-stabilizing agent is composed of a halogen ion and/or silver ion, or a compound which is capable of dissociating a halogen ion and/or silver ion.

This invention also provides (12) an ion sensor plate as set forth in the aforementioned item (10) or (11) wherein said electric potential-stabilizing agent is silver halide.

This invention also provides (13) an ion sensor plate as set forth in any of the aforementioned item (10) or (11) wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an ion sensitive material which is higher than that is required for responding to said specific ion.

This invention also provides (14) an ion sensor plate as set forth in the aforementioned item (10) wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an electric potential-stabilizing agent which is higher than that is required for eliminating said disturbance by said anion.

This invention also provides (15) an ion sensor plate as set forth in the aforementioned item (10) or (11), wherein at least part of said closed channel for supplying said test liquid among these closed channels for supplying said test liquid and said reference liquid is provided with a coated film of surfactant which is capable of adding said surfactant to said test liquid as said test liquid passes through said closed channels for supplying said test liquid.

This invention also provides (16) an ion sensor plate as set forth in the aforementioned item (10) or (11) wherein said ion sensitive membrane contains at least a matrix, a plasticizer for plasticizing said matrix and an ion sensitive material, the content of said plasticizer being 65 to 80% by weight based on said ion sensitive membrane.

This invention also provides (17) an ion sensor plate as set forth in the aforementioned item (10) or (11) wherein said silver halide layer formed on said silver layer is a modified silver halide layer which is modified in such a manner that the atomic ratio of silver and halogen: Ag/Cl is at least 1.2.

This invention also provides (18) an ion sensor plate as set forth in the aforementioned item (17) wherein a particle diameter of said silver halide and of said silver in said modified silver halide layer is at most 1 μm.

The inventions related to the ion sensor and ion sensor plate as set forth in the aforementioned items (1) to (5) and (10) to (14) are all directed to improve the precision of measurement and at the same time, to reduce the time required for stabilizing the measured value. The inventions related to the ion sensor and ion sensor plate as set forth in the aforementioned items (6) and (15) are all directed to minimize any influence on the measured value of ion concentration that might be brought about by a special component contained in the blood for instance.

The inventions related to the ion sensor and ion sensor plate as set forth in the aforementioned items (7) and (16) are all directed to provide an ion sensitive membrane which is uniform in composition, large in contacting area with the underlying layer, and excellent in electric potential-stabilizing efficiency of the potential-stabilizing agent, thereby to improve the initial characteristics immediately after the manufacture thereof, to minimize the inconsistency of the characteristics and to improve the measurement precision. The inventions related to the ion sensor and ion sensor plate as set forth in the aforementioned items (8), (9), (17) and (18) are all directed to reduce electric resistance at the interface between the ion sensitive membrane and the silver/silver halide electrode.

DETAILED DESCRIPTION OF THE INVENTION

This invention will be explained further with reference to the following preferred embodiments of this invention.

Figure 2:
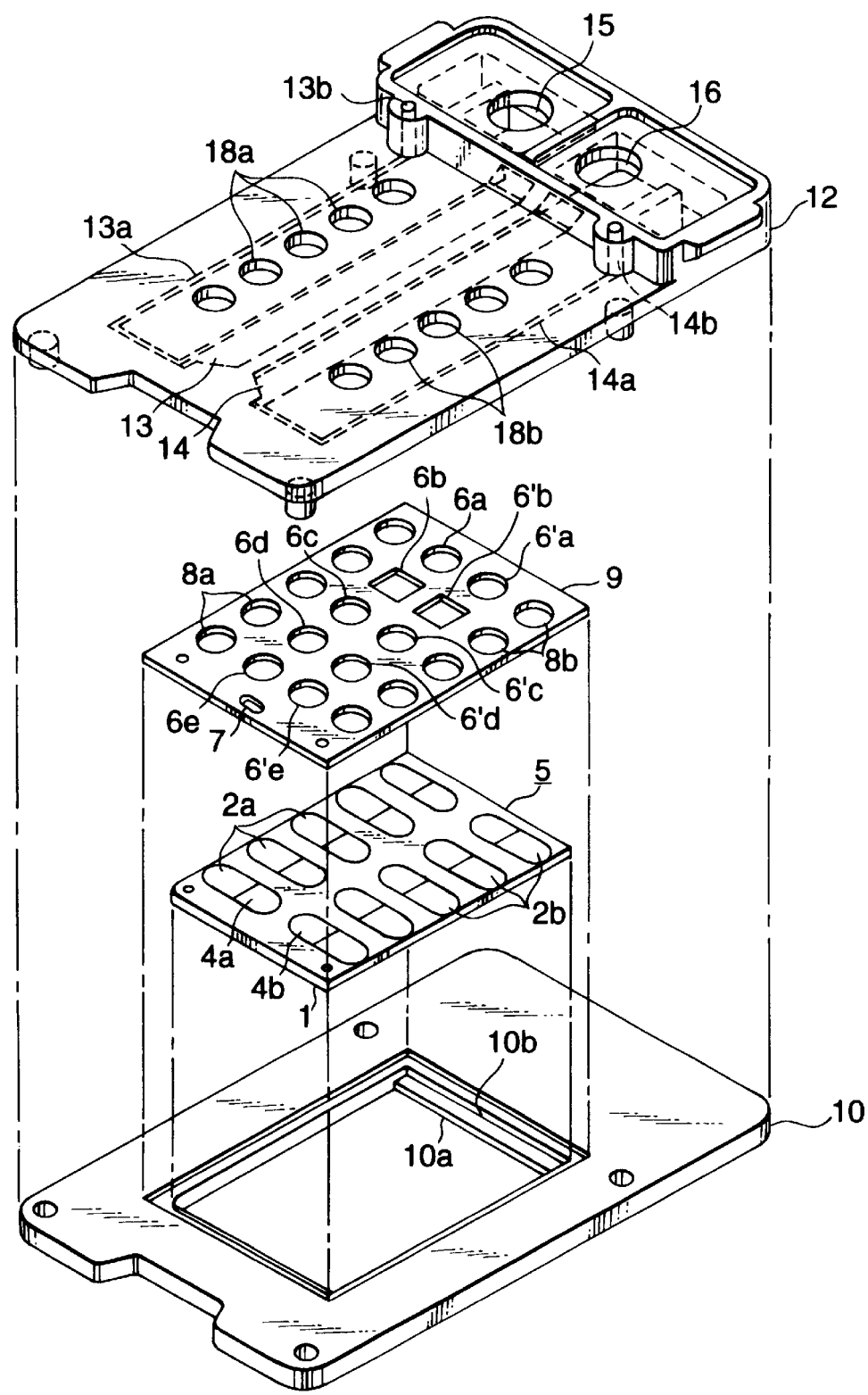
FIG. 2 is an exploded perspective view of the multi-ion sensor plate shown in FIG. 1.

In the manufacture of an ion sensitive electrode, a combined body consisting of a multi-ion sensor plate main body 5 and a channel body 9 is fabricated at first as shown in FIG. 2. Then, a resinous solution for forming an ion sensitive membrane which is sensitive to a specific ion and composed of a polyvinyl chloride-based resin, a plasticizer, an ion sensitive material, an electrical potential-stabilizing agent, and, if required, a salt such as an anion scavenger is dripped into the through-holes 6*a* and 6′*a* for instance among the through-holes 6*a* to 6*e* and 6′*a* to 6′*e*, the resinous solution thus dripped being subsequently allowed to dry thereby to form an ion sensitive membrane, thus obtaining an ion sensitive electrode for detecting a specific ion.

Figure 1:
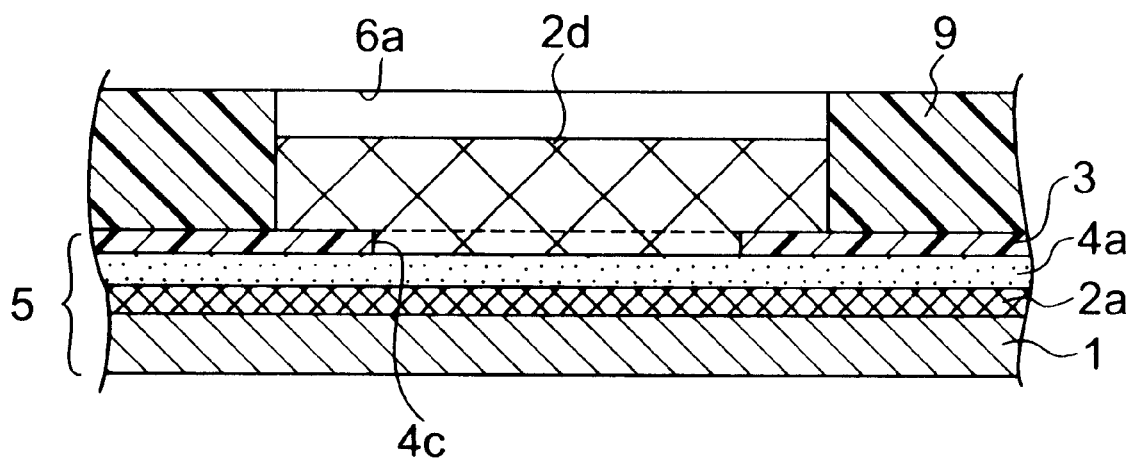
FIG. 1 is a cross-sectional view showing part of the multi-ion sensor plate of Example 1 to which an ion sensor plate of this invention is applied.

FIG. 1 illustrates a cross-sectional view of the peripheral portion around the electrode disposed on the test liquid-feeding side. Referring to FIG. 1, the reference numeral 1 denotes a glass-epoxy resin substrate; 2*a*, a test liquid-measuring electrode; 4*a*, a silver chloride layer; 3, an insulating film covering the silver chloride layer 4*a* except the portion which coincides with the through-hole 6*a* and the outer edge portion of the electrode, thus covering the surface of multi-ion sensor plate main body 5 (the same with other electrodes not shown in FIG. 1); 4*c*, a window; 9, a channel body; 6*a*, a through-hole; and 2*d*, an ion sensitive membrane.

Likewise, various different kinds of resinous solution for forming different kinds of ion sensitive membrane are then dripped into each pair of the through-holes 6*b* and 6′*b*, 6*c* and 6′*c*, 6*d* and 6′*d*, and 6*e* and 6′*e*, these resinous solutions thus dripped being subsequently allowed to dry thereby obtaining various kinds of ion sensitive electrode each provided with a specific kind of ion sensitive membrane.

Then, the combined body consisting of the multi-ion sensor plate main body 5 and the channel body 9 as shown in FIG. 2 is fitted in the recessed portions 10*a* and 10*b* of the lower cell 10 which is made of a transparent acrylic resin. Thereafter, an upper cell 12 made of a transparent acrylic resin is superimposed, via a double coated adhesive tape, on this lower cell 10 thereby bonding these cells with each other and packaging the aforementioned combined body.

Thereafter, a test liquid and a reference liquid are introduced by means of a syringe into the test liquid inlet portion 15 and the reference liquid inlet portion 16 of the multi-ion sensor plate of this structure, respectively. These test liquid and reference liquid are then allowed to pass through the channels 13, 14, respectively, thus supplying these liquids to the ion sensitive electrodes in the through-holes 6*a* to 6*e* and 6′*a* to 6′*e*, respectively. These liquids thus supplied are then allowed to contact with each other at the liquid junction portion 7 thereby allowing these liquids to take an electrically conductive state. Thereafter, the terminals of measuring apparatus (not shown) are inserted into terminal-introducing ports 18a and 18b so as to contacting them with each of the electrodes, thus measuring the concentrations of five different kinds of ion in the test liquid.

As for the electric potential-stabilizing agent or a material pertinent to the electric potential-stabilizing agent that may be incorporated into the ion sensitive membrane, the following measures may be taken. Namely, (1) $Ag^+$ and/or $X^-$ is incorporated into the ion sensitive membrane at a concentration which corresponds at least to the concentration of $Ag^+$ or $X^-$ at the moment of dissociation equilibrium of: $AgX \leftrightarrows Ag^+ + X^-$ (wherein X is a halogen atom, the same hereinafter); (2) If the $X^-$ is incorporated into the ion sensitive membrane, and the quantity of the $X^-$ incorporated becomes excessive as compared with the concentration at the moment of dissociation equilibrium thereof, the salt of silver halide AgX would be turned into $AgX^{1-n}_n$ complex, thus rendering it to be easily dissolved into the ion sensitive membrane. Therefore, AgX should be dissolved into the ion sensitive membrane up to the saturation concentration thereof; (3) If an anion scavenger (such as Na-TPB (sodium tetraphenyl borate), K-TCPB (potassium tetrakis-p-chlorophenyl borate)) is incorporated into the ion sensitive membrane so as to protect the ion sensitive membrane from being disturbed by an anion originating from the test liquid or the reference liquid, the anion scavenger may be associated with $Ag^{30}$, $X^-$ or $AgX^{1-n}_n$ complex, provided that these ions or complex are existed in the ion sensitive membrane at a high concentration, thus forming an ion pair and hence reducing the effective concentration of these ions and complex. Therefore, an ionophore constituting an ion sensitive material in the ion sensitive membrane should be incorporated into the ion sensitive membrane in advance; (4) Although it differs in concept from the aforementioned measures (1) to (3), the aforementioned anion scavenger is incorporated into the ion sensitive membrane at a concentration higher than that is enough to eliminate the anion originating from the test liquid or the reference liquid. For example, when the Na-TPB is employed, it should be incorporated at a concentration of at least $1 \times 10^{-2}$ M/L (mole/liter) ($1 \times 10^{-2}$ M/L or more).

The aforementioned measures (1) to (3) may be employed in combination.

When the measures (1) are adopted, the dissociation equilibrium of: $AgX \leftrightarrows Ag^+ + X^-$ can be fixed, thus making it possible to disregard not only any slight inconsistency in dissolution quantity of $Ag^+$ or $X^-$ of the AgX layer of the electrode of individual multi-ion sensor plate into the ion sensitive membrane, but also any change in dissolution quantity of these $Ag^+$ or $X^-$ due to changes in environmental conditions. As a result, the electric potential to be generated at the interface between the AgX layer and the ion sensitive membrane can be controlled within an extremely limited range.

Further, according to the measure (2), since AgX is mixed into the ion sensitive membrane in advance, it is possible to prevent the AgX in the AgX layer from dissolving into the ion sensitive membrane after the AgX is turned into $Ag^{1-n}_n$ complex, thus making it possible to fix the dissociation equilibrium of: $AgX \leftrightarrows Ag^+ + X^-$. Namely, if AgX is not mixed into the ion sensitive membrane in advance thereby allowing the AgX to gradually dissolve into the ion sensitive membrane, not only it is impossible to fix the dissociation equilibrium of: $AgX \leftrightarrows Ag^+ + X^-$ at the interface between the AgX layer and the ion sensitive membrane, but also the AgX constituting an underlying layer may be completely dissolved in a long period of time thereby to expose the Ag layer, thus inviting the possibility of generating an error in generated electric potential due to a difference in equilibrium potential between the AgX and the metallic Ag. According to the measures (2), this problem can be avoided. By the way, it is known that when a salt of silver halide AgX is dissolved into a solution containing $X^-$ in high concentration, the salt is generally dissolved in the form of $AgX^{1-n}_n$ complex into the solution.

When the measures (3) are adopted, the cation of the aforementioned associated ion pair can be chelated with ionophore, so that the effective concentration, in the ion sensitive membrane, of so-called potential-determining ion of $Ag^+$, $X^-$ and $AgX^{1-n}_n$ complex, as well as of the complex can be increased thereby making it possible to fix the dissociation equilibrium of: $AgX \leftrightarrows Ag^+ + X^-$.

Na-TPB for instance is known to react with alkaline metals excluding Na and Li or with a monovalent metal ion $M^+$ thereby to produce M-TPB precipitate which is hardly soluble. Accordingly, it may be conceivable that it also reacts with $Ag^+$ thereby to produce Ag-TPB. However, if Na-TPB is incorporated into the ion sensitive membrane at a concentration as set forth in the aforementioned measurements (4), the interstitial $Ag^+$ of the AgX layer or the $Ag^+$ that has been generated from dissolution of the AgX layer is caused to react with the Na-TPB at the interface between the AgX layer ad the ion sensitive membrane thereby to produce Ag-TPB. As a result, the AgX existing at this interface is replaced by this Ag-TPB, and hence the electric potential to be generated can be determined by the dissociation equilibrium of: $Ag\text{-}TPB \leftrightarrows Ag^+ + TPB^-$. However, since TPB is incorporated into the ion sensitive membrane at a high concentration, i.e. $1 \times 10^{-2}$ M/L or more, the solubility of $Ag^+$ or $TPB^-$ into the ion sensitive membrane can be suitably controlled, thus making it possible to fix the dissociation equilibrium of: $Ag\text{-}TPB \leftrightarrows Ag^+ + TPB^-$ and at the same time, to stabilize the electric potential to be generated. In this case, since any cause for obstructing the equilibrium of $AgX \leftrightarrows Ag^+ + X^-$ is no more existed, the problems to be solved by means of the aforementioned measures (1) and (2) can be eliminated.

As for the supply source of $Cl^-$, trioctylmethyl ammonium chloride may be employed. It is also possible to employ, as a supply source of $Cl^-$, ammonium salts represented by the general formula: $R_4N^+Cl^-$ (wherein R is alkyl group, the same hereinafter), obtaining almost the same effect as that of trioctylmethyl ammonium chloride. Instead of the aforementioned ammonium salts, phosphonium salts represented by the general formula: $R_4P^+Cl^-$ may be also employed as a supply source of $Cl^-$.

The X may be Br or I instead of Cl, obtaining almost the same effect as that of Cl. Specific examples of such compounds can be represented by the general formulas such as $R_4N^+Br^-$, $R_4N^+I^-$, $R_4P^+Br^-$, $R_4P^+I^-$, etc.

As for the aforementioned polyvinyl chloride-based resin, vinyl chloride resin, copolymers comprising vinyl chloride and at least one kind of vinyl type monomer such as vinyl acetate, vinyl alcohol, carboxyl-containing monomer, etc. As for the aforementioned plasticizer, a phthalic acid-based plasticizer, an aliphatic dibasic acid-based plasticizer, an ether comprising substituted or unsubstituted phenol and higher alcohol, etc. These plasticizers may be employed at any suitable ratio.

Figure 3:
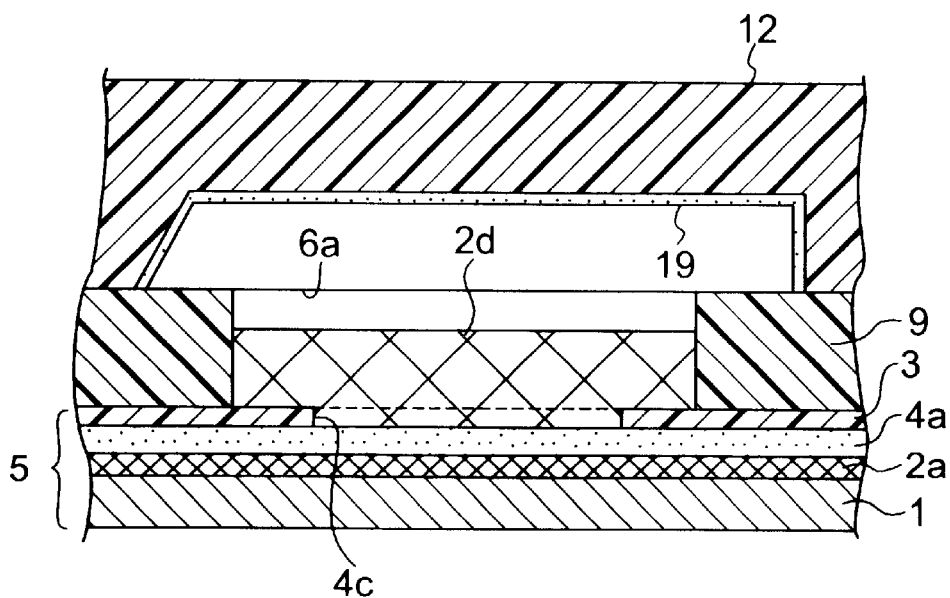
FIG. 3 is a cross-sectional view showing part of the multi-ion sensor plate of Example 2 of this invention.

In another example of this invention, as shown in FIG. 3 where the same parts as those of other FIGS. are referred to by the same numbers, the upper cell 12 may be constructed such that at least the test liquid-feeding passageway for supplying a test liquid among the test liquid-feeding passageway and the reference liquid-feeding passageway is provided with a surfactant-coated film 19 which is capable of incorporating a suitable concentration of surfactant into the test liquid depending on the kind of surfactant as the test liquid passes therethrough. By the way, 4a is a silver halide layer.

After a multi-ion sensor plate provided with the aforementioned upper cell 12, and having a structure as shown in FIG. 2 is assembled in this manner, a test liquid and a reference liquid are introduced by means of a syringe into the test liquid inlet portion 15 and the reference liquid inlet portion 16 of the multi-ion sensor plate, respectively. These test liquid and reference liquid are then allowed to pass through the channels 13, 14, respectively, thus supplying these liquids to the ion sensitive electrodes in the through-holes 6a to 6e and 6'a to 6'e, respectively. These liquids thus supplied are then allowed to contact with each other at the liquid junction portion 7 thereby allowing these liquids to take an electrically conductive state. Thereafter, the terminals of measuring apparatus (not shown) are inserted into terminal-introducing ports 18a and 18b so as to contacting them with each of the electrodes, thus measuring the concentrations of five different kinds of ion in the test liquid.

When the passageway of the multi-ion sensor plate is provided with a surfactant-coated film, the surfactant is incorporated into the test liquid or the reference liquid, thereby improving the dispersibility of hemocyte or protein. As a result, it is possible to prevent hemocyte or protein from being precipitated on the ion sensitive membrane, and hence to avoid the surface of the ion sensitive membrane from being covered by the hemocyte or protein, thus minimizing the phenomenon that might occur when the dispersibility of hemocyte or protein is poor, i.e. the phenomenon where the ions in the test liquid are prevented from contacting with the ion sensitive membrane.

In the foregoing embodiment, the passageways 13 and 14 are coated with a surfactant. However, it is also possible to employ even a multi-ion sensor plate where the upper cell shown in FIG. 2 is employed as it is, except that the aforementioned surfactant is not coated on the passageways. In this case, the measurement with this multi-ion sensor plate is performed in the same manner as described above by making use of a mixture containing a surfactant which has been incorporated into at least the test liquid among the test liquid and the reference liquid at a suitable concentration depending on the kind of surfactant.

Since the surfactant is simply coated on the passageways or incorporated into a test liquid, the operation thereof is very easy and the structure of the sensor is also simple, so that this invention can be applied to the conventional ion sensor and ion sensor plate without substantially altering the manner of employment or the manufacturing steps.

By the way, the term "surfactant" may be understood as meaning "surfactant for maintaining the dispersibility of materials (hemocyte or other similar substances) included in a test liquid, thereby preventing the materials from being precipitated (settled)".

Further, when a surfactant is coated on the passageway of the reference liquid so as to allow the surfactant to be added to the reference liquid as the reference liquid passes through the passageway thereof, the condition for comparing with the case where the passageway for the test liquid is also coated similarly with the surfactant can be made consistent.

Additionally, when a surfactant is included in advance in the reference liquid, the condition for comparing with the case where the surfactant is included in the test liquid can be made consistent.

As for specific examples of the surfactant, it is possible to employ alkyl sulfate ester, alkylbenzene sulfonate, alkylnaphthalene sulfonate, alkylsulfosuccinate, alkyldiphenyl ether disulfonate, alkyl phosphate, polyoxyethylene alkyl or alkyl allyl sulfate ester, naphthalene sulfonic acid/formalin condensate, special polycarbonic acid type polymer surfactant, polyoxyethylene alkylphosphate, other kinds of anionic surfactant, polyoxyethylene alkylether, polyoxyethylene alkylallylether, polyoxyethylene derivatives, oxyethylene/oxypropylene block polymer, sorbitan aliphatic acid ester, polyoxyethylene sorbitan aliphatic acid ester, polyoxyethylene sorbitol aliphatic acid ester, glycerine aliphatic acid ester, polyoxyethylene aliphatic acid ester, polyoxyethylene alkylamine and other kinds of nonionic surfactant, alkylamine salt, quaternary ammonium salt, alkylbetaine, amine oxide and other kinds of cationic surfactant, and amphoteric surfactant.

If a surfactant containing an ion to be detected is employed, it may become difficult to obtain a real value of the ion concentration in a test liquid. Therefore, the employment of such a surfactant is undesirable.

In another embodiment of this invention, a resinous solution containing a plasticizer at ratio of 65 to 80% by weight, preferably 65 to 78% by weight, more preferably 70 to 75% by weight based on the total of non-volatile matters of the solution (the entire weight of ion sensitive membrane after the drying thereof) for forming an ion-sensitive film responding to a specific ion is dripped into the through-holes 6a and 6'a of the channel body shown in FIG. 2, and then dried to form an ion-sensitive film for a specific ion, thereby forming an ion sensitive electrode.

Referring to FIG. 1, the reference symbol 2d denotes an ion sensitive membrane which is obtained by the dripping of the aforementioned resinous solution. The reference symbol 4a in FIG. 1 denotes a silver halide layer. Other reference symbols represent constituent members as seen in the explanation of FIG. 1.

Likewise, various different kinds of resinous solution (the content of the plasticizer is the same as explained above) for forming different kinds of ion sensitive membrane are then dripped into each pair of the through-holes 6b and 6'b, 6c and 6'c, 6d and 6'd, and 6e and 6'e, these resinous solutions thus dripped being subsequently allowed to dry thereby obtaining various kinds of ion sensitive electrode each provided with a specific kind of ion sensitive membrane.

Thereafter, a test liquid and a reference liquid are respectively introduced by means of a syringe into the test liquid inlet portion 15 and the reference liquid inlet portion 16 of the multi-ion sensor plate provided with the aforementioned ion sensitive electrodes, having a structure as shown in FIG. 2 and assembled in this manner. These test liquid and reference liquid are then allowed to pass through the channels 13, 14, respectively, thus supplying these liquids to the ion sensitive electrodes in the through-holes 6a to 6e and 6'a to 6'e, respectively. These liquids thus supplied are then allowed to contact with each other at the liquid junction portion 7 thereby allowing these liquids to take an electrically conductive state. Thereafter, the terminals of measuring apparatus (not shown) are inserted into terminal-introducing ports 18a and 18b so as to contacting them with each of the electrodes, thus measuring the concentrations of five different kinds of ion in the test liquid.

When the resinous solution is formulated in this manner, the plasticizer contained in the solution for forming an ion sensitive membrane functions as a so-called poor solvent which is relatively low in solubility to a polyvinyl chloride-based resin, so that by increasing the content of the plasticizer in relative to the resin, the dispersibility of the resin and other additives in relative to the plasticizer can be enhanced. Accordingly, even if a coated film is formed by the process comprising the steps of dripping of this solution and air-drying the dripped solution thereby allowing the solvent to evaporate, a convection can be hardly generated in the surface or interior of the coated film, thus making it possible to prevent the aforementioned orange peel from being generated. Namely, the dispersibility of these ionophore, salts, aforementioned electric potential-stabilizing material that have been added can be excellently maintained, and at the same time, the fluidity of the coated film can be maintained, thus making it possible to obtain a film of more uniform composition.

When an ion sensitive membrane exhibiting an excellent dispersibility of the electric potential-stabilizing material, ionophore, etc. and having a uniform composition is formed in this manner, the penetrated state of water contained in the test liquid and in the reference liquid can be maintained uniform, thus minimizing the inconsistency, if any, of measured values.

The ion sensitive membrane containing a large quantity of a plasticizer in relative to polyvinyl chloride resin as mentioned above is excellent in flexibility, thus increasing the contacting area thereof with the underlying silver chloride layer. Accordingly, the electric potential-stabilizing material, ionophore, etc. that have been included in the ion sensitive membrane can be effectively acted so as to control the ion sensitive membrane in such a manner that the chemical equilibrium of the silver halide, etc. can be stabilized. As a result, the initial characteristics of the ion sensor can be improved, and at the same time, the electric potential at the interface between the silver halide layer and the ion sensitive membrane can be readily stabilized, thus making it possible to minimize the inconsistency of the initial characteristics of the ion sensor as well as the inconsistency of the values measured.

If the stabilization of the initial characteristics of the sensor can be finished within a shorter period of time, the examination thereof can be also finished within a shorter period of time. Further, if the inconsistency of the initial characteristics of the sensor is minimized, the yield of the sensor can be improved.

In further another embodiment of this invention, the silver chloride layer 4a shown in FIG. 1 is replaced by a modified silver chloride layer 4a (details thereof is not shown). This modified silver chloride layer 4a can be formed by a process wherein a silver plating is performed on the copper foil of the test liquid-measuring electrode 2a, and then a silver halide layer formed of particles having a diameter of 1 $\mu$m or slightly larger than 1 $\mu$m is formed by means of anodic oxidation employing electrolysis, the resultant silver halide layer being subsequently reduced so as to increase the ratio of silver by making use of physical reduction means employing ultraviolet ray or a beam involving ultraviolet ray which is capable of reducing silver ion, or by making use of etching means employing a solution of a chloride. Although it is not shown in the drawings, other modified silver halide layers 4a and 4b shown in FIG. 2 can be formed in the same manner as described above.

When ultraviolet ray or a beam involving ultraviolet ray is irradiated onto the silver halide layer, the silver in the silver halide layer is reduced and made free. The halogen ion to be employed in this case should preferably be chloride ion, which is commonly employed, readily evaporated in the form of volatile gas, and easy in handling.

When silver ion is reduced, it is turned into silver. Therefore, when halogen ion is removed or when the grain boundary of the silver is dissolved through an etching, the diameter of the silver halide crystal of the silver halide layer can be controlled to not more than 1 $\mu$m, preferably not more than 0.8 $\mu$m, more preferably not more than 0.7 $\mu$m. It is also possible to control the grain size of silver by means of reduction. It is also possible to increase the atomic ratio between the silver and halogen (Ag/X) of the crystals of the silver chloride layer, i.e. the atomic ratio (Ag/X) can be controlled to not less than 1.2, preferably not less than 1.3, more preferably not less than 1.6.

When the grain size of the silver halide layer is minimized in this manner, the surface area thereof can be increased, thus enlarging the contacting area thereof with the ion sensitive membrane. Further, when the ratio of this reduced silver is increased, the conductivity of electron can be improved, thus making it possible to decrease the electric resistance thereof.

Next, a resinous solution containing a plasticizer at ratio of 65 to 80% by weight, preferably 65 to 78% by weight, more preferably 70 to 75% by weight based on the total of non-volatile matters of the solution (the entire weight of ion sensitive membrane after the drying thereof) for forming an ion-sensitive film responding to a specific ion is dripped into the through-holes 6a and 6'a of the channel body shown in FIG. 2, and then dried to form an ion-sensitive film for a specific ion, thereby forming an ion sensitive electrode.

Referring to FIG. 1, the reference symbol 2d denotes an ion sensitive membrane which is obtained by the dripping of the aforementioned resinous solution. The reference symbol 4a in FIG. 1 denotes a silver halide layer. Other reference symbols represent constituent members as seen in the explanation of FIG. 1.

Likewise, various different kinds of resinous solution (the content of the plasticizer is the same as explained above) for forming different kinds of ion sensitive membrane are then dripped into each pair of the through-holes 6b and 6'b, 6c and 6'c, 6d and 6'd, and 6e and 6'e, these resinous solutions thus dripped being subsequently allowed to dry thereby obtaining various kinds of ion sensitive electrode each provided with a specific kind of ion sensitive membrane.

When an electric potential-stabilizing agent or a material pertinent to the electric potential-stabilizing agent is incorporated into the ion sensitive membrane in this manner, the electric potential at the interface between the ion sensitive membrane and the silver halide layer can be stabilized.

When a plasticizer is incorporated into the ion sensitive membrane, the resultant ion sensitive membrane containing a large quantity of the plasticizer in relative to polyvinyl chloride resin is excellent in flexibility. As a result, it becomes possible to enable the ion sensitive membrane to conform to the fine rugged surface of the modified silver halide layer whose surface area is increased by minimizing the grain diameter of the silver halide layer as mentioned above, so that the contacting area of the ion sensitive membrane with the modified silver halide layer would be increased, thus making it possible to minimize the electric resistance at the interface therebetween.

Thereafter, a test liquid and a reference liquid are respectively introduced by means of a syringe into the test liquid inlet portion 15 and the reference liquid inlet portion 16 of the multi-ion sensor plate provided with the aforementioned ion sensitive electrodes, having a structure as shown in FIG. 2 and assembled in this manner. These test liquid and reference liquid are then allowed to pass through the channels 13, 14, respectively, thus supplying these liquids to the ion sensitive electrodes in the through-holes 6a to 6e and 6'a to 6'e, respectively. These liquids thus supplied are then allowed to contact with each other at the liquid junction portion 7 thereby allowing these liquids to take an electrically conductive state. Thereafter, the terminals of measuring apparatus (not shown) are inserted into terminal-introducing ports 18a and 18b so as to contacting them with each of the electrodes, thus measuring the concentrations of five different kinds of ion in the test liquid.

Next, preferable examples of this invention will be explained in detail as follows.

EXAMPLE 1

A resinous solution for forming an ion sensitive membrane was prepared by simultaneously mixing the following components.

| | |
|---|---|
| GKT (matrix) (polyvinyl chloride-based resin available from Denki Kagaku Kogyo K.K.; i.e. a copolymer of; vinyl chloride:vinyl acetate:vinyl alcohol = 90:4:6) | 0.13 g |
| NPOE (2-nitrophenyloctyl ether) (plasticizer) | 0.2 g |
| Trioctylemethyl ammonium chloride (Cl⁻source) | 0.808 mg |
| Bis (12-crown-4) (Na ionophore) | 13.26 mg |
| Na-TPB (sodium tetrakisphenyl borate) (anion scavenger) | 0.39 mg |
| THF (tetrahydrofran) (solvent) | 2 mL |

This resinous solution for forming an ion sensitive membrane was dripped onto the silver chloride layers 4a and 4b through the through-holes 6a and 6'a as explained in reference to FIGS. 1 and 2, whereby forming coated layers which were then air-dried to form a sodium sensitive film functioning as an ion-sensitive film 2d.

The multi-ion sensor plate having a structure shown in FIGS. 1 and 2 was prepared in total of 20 pieces. Then, by making use of the multi-ion sensor plates immediately after the manufacture thereof and also the multi-ion sensor plates which were left to stand for 30 days after the manufacture thereof, the electric potential of each sample sensor plate was measured according to the aforementioned measuring method using an aqueous solution containing 140 mM NaCl as a test liquid, and a prescribed reference liquid as a reference liquid. Subsequently, the standard deviation of the measured values was calculated, the results being shown in Table 1 as "Initial Value" and "Value after 30 days".

This example belongs to the case where the aforementioned measures (1) and (2) were co-used.

By the way, when Bis(12-crown-4) (ionophore) is employed at a ratio of standard quantity of 2 mg per 0.2 g of plasticizer (about 15 mM), it belongs to the aforementioned measures (1). This ratio of 13.26 mg/0.2 g plasticizer corresponds to a concentration of about 100 mM.

EXAMPLE 2

A resinous solution for forming an ion sensitive membrane was prepared using the following components.

| | |
|---|---|
| GKT (matrix) (the same copolymer as Example 1) | 0.13 g |
| NPOE (2-nitrophenyloctyl ether) (plasticizer) | 0.2 g |
| Vasophenanthroline (chelating agent) | 4 mg |
| Silver chloride powder | mg |
| Bis (12-crown-4) (Na ionophore) | 13.26 mg |
| Na-TPB (sodium tetrakisphenyl borate) (anion scavenger) | 0.39 mg |
| THF (tetrahydrofran) (solvent) | 2 mL |

This resinous solution for forming an ion sensitive membrane was prepared by a process wherein vasophenanthroline and silver chloride powder were added to NPOE to obtain a mixture, which was then stirred for 12 hours. Subsequently, the resultant supernatant was taken out and then mixed with GKT, Na-TPB, Bis(12-crown-4) and THF, thereby allowing these additives to be sufficiently dissolved in the supernatant.

By the way, the vasophenanthroline is employed for chelating Ag⁺ from the silver chloride powder thereby releasing Cl⁻.

Multi-ion sensor plates each provided with a sodium ion sensitive membrane were prepared in the same manner as explained in Example 1 except that this resinous solution for forming an ion sensitive membrane was employed.

The multi-ion sensor plate having a structure shown in FIGS. 1 and 2 was prepared in total of 20 pieces. Then, by making use of the multi-ion sensor plates in the same manner as explained in Example 1, the electric potential corresponding to a sodium ion concentration was measured. Subsequently, the standard deviation was calculated from the measured values, the results being shown in Table 1.

This example belongs to the case where the aforementioned measures (1) and (3) were co-used.

EXAMPLE 3

Multi-ion sensor plates each provided with a sodium ion sensitive membrane were prepared in the same manner as explained in Example 1 except that a resinous solution for forming an ion sensitive membrane was prepared by the following procedures.

Then, by making use of the multi-ion sensor plates in the same manner as explained in Example 1, the electric potential corresponding to a sodium ion concentration was measured. Subsequently, the standard deviation was calculated from the measured values, the results being shown in Table 1.

By making use of the same composition as shown in Example 1, resinous solution for forming an ion sensitive membrane was prepared by a process wherein trioctylmethyl ammonium chloride was dissolved in NPOE to obtain a solution, to which AgCl powder was added and stirred for 12 hours. Subsequently, the resultant supernatant of the mixed solution was taken out and then mixed with GKT, Na-TPB, Bis(12-crown-4) and THF, thereby allowing these additives to be sufficiently dissolved in the supernatant.

This example belongs to the case where the aforementioned measures (1), (2) and (3) were co-used.

EXAMPLE 4

A resinous solution for forming an ion sensitive membrane was prepared by simultaneously mixing the following components.

| | |
|---|---|
| GKT (matrix) (the same copolymer as Example 1) | 0.13 g |
| NPOE (2-nitrophenyloctyl ether) (plasticizer) | 0.2 g |
| Bis (12-crown-4) (Na ionophore) | 13.26 mg |
| Na-TPB (sodium tetrakisphenyl borate) (anion scavenger; 1 × 10$^{-2}$M) | 0.39 mg |
| THF (tetrahydrofran) (solvent) | 2 mL |

Multi-ion sensor plates each provided with a sodium ion sensitive membrane were prepared in the same manner as explained in Example 1 except that this resinous solution for forming an ion sensitive membrane was employed.

Then, by making use of the multi-ion sensor plates in the same manner as explained in Example 1, the electric potential corresponding to a sodium ion concentration was measured. Subsequently, the standard deviation was calculated from the measured values, the results being shown in Table 1.

This example belongs to the case where the aforementioned measures (4) was employed.

Comparative Example 1

Multi-ion sensor plates each provided with a sodium ion sensitive membrane were prepared in the same manner as explained in Example 1 except that trioctylemethyl ammonium chloride was not employed.

Then, by making use of the multi-ion sensor plates in the same manner as explained in Example 1, the electric potential corresponding to a sodium ion concentration was measured. Subsequently, the standard deviation was calculated from the measured values, the results being shown in Table 1.

TABLE 1

| | STANDARD DEVIATION | |
|---|---|---|
| | INITIAL VALVE | AFTER 30 DAYS |
| Ex. 1 | 0.1 | 0.5 |
| Ex. 2 | 0.2 | 0.5 |
| Ex. 3 | 0.2 | 0.2 |
| Ex. 4 | 0.2 | 0.2 |
| COMP. Ex. 1 | 1.3 | 2.0 |

As seen from the results shown in Table 1, all of the results obtained according to any of Examples were more excellent in precision as compared with the results obtained according to Comparative Example, i.e. as compared with Comparative Example, the standard deviation or the inconsitency in these Examples was ⅙ or less in the initial value, and ¼ or less even after 30 days. In particular, the standard deviation in Example 3 was 1/10 as compared with Comparative Example, thus indicating an excellent precision. It will be seen from these results that when an electric potential-stabilizing agent or a material pertinent to the electric potential-stabilizing agent is incorporated into an ion sensitive membrane, the inconsistency in electric potential at the interface between the ion sensitive membrane and the silver chloride layer can be reduced, as compared with the ion sensitive membrane not containing an electric potential-stabilizing agent and like, to at least half, preferably at least 20% in the initial value based on the standard deviation, and to at least half, preferably at least 25% in the value after 30 days based on the standard deviation. Furthermore, when an anion scavenger is employed as an electric potential-stabilizing agent, the standard deviation can be reduced to at least 10% of that of an ion sensitive membrane not containing an electric potential-stabilizing agent and like.

The expression of the invention recited in the aforementioned item (1) may be replaced by the expression; "at least one kind of AgX dissociation equilibrium-constituting material (a material capable of dissociating an ion, if the constituent material is ion) is incorporated into an ion sensitive membrane".

EXAMPLE 5

0.8 mg of quarternary amine salt (supply source of Cl−) such as trioctylmethyl ammonium chloride was added to 2 g of DOS (sebacic acid(2-ethylhexyl)) (plasticizer) to obtain a mixture, to which 10 mg of AgCl powder (electric potential-stabilizing agent) was added and stirred. Then, 250 mg of the supernatant of this mixture was taken up and mixed with 155 mg of PVC (a copolymer of; vinyl chloride:vinyl acetate:vinyl alcohol=90:4:6, which was available from Denki Kagaku Kogyo K.K.), with 8.6 mg of ETH1001 (ionophore for detecting calcium ion), with 1.24 mg of K-TCPB (potassium tetrakis(p-chlorophenyl) borate; Dojin Kagaku Co., Ltd., anion scavenger), and with 250 mL of THF (tetrahydrofran) (solvent) to obtain a resinous solution for preparing an ion sensitive membrane.

Although the aforementioned supernatant contained quaternary amine salt and AgCl, it could be disregarded as the quantity thereof was minimal, thus making it possible to assume this supernatant as being 250 mg of a plasticizer, and to assume it as being about 60% by weight based on the non-volatile matters (ion sensitive membrane).

This resinous solution for forming an ion sensitive membrane was dripped onto the silver chloride layers 4a and 4b through the through-holes 6a and 6'a as explained in reference to FIGS. 1 and 2, whereby forming coated layers which were then air-dried to form a sodium ion sensitive membrane functioning as an ion-sensitive film 2d.

Then, as shown in FIG. 3, the inner surfaces of the passageways 13 and 14 of the upper cell 12 (on the inner surface of the passageway 13 is shown, the structure is the same in the case of the inner surface of the passageway 14) were coated with an ethanol solution containing KF-6004 (terminal-reactive silicone oil; nonionic surfactant available from Shin-Etsu Chemical Co., Ltd.) at a concentration of 0.1 g/L, and dried to obtain a coated surfactant film 19.

A multi-ion sensor plate having a structure as shown in FIGS. 2 and 3 was prepared in the same manner as explained above except that the aforementioned procedures were performed.

Then, by making use of this multi-ion sensor plate, the sodium ion concentration was measured employing a plurality of test liquids having varied values of hematocrit % (Hct %) in the blood. The results being shown in FIG. 4 by a solid line.

The samples of the test liquid were prepared using the whole blood of house (thoroughbred), which was subsequently subjected to centrifugal separation so as to separate it into hemocyte and plasma, and then the quantity of plasma was varied. The samples were then measured by means of a capillary method, thereby obtaining values of Hct %, which were found varied as shown in FIG. 4.

Comparative Example 2

Calcium ion concentration was measured in the same manner as explained in Example 5, except that the surfactant was not. coated on the inner surfaces of the passageways 13 and 14 of the upper cell 12, i.e. the conditions of the inner surfaces thereof were the same as those obtained immediately after the manufacture thereof. The results being shown in FIG. 4 by a dotted line.

Figure 4:
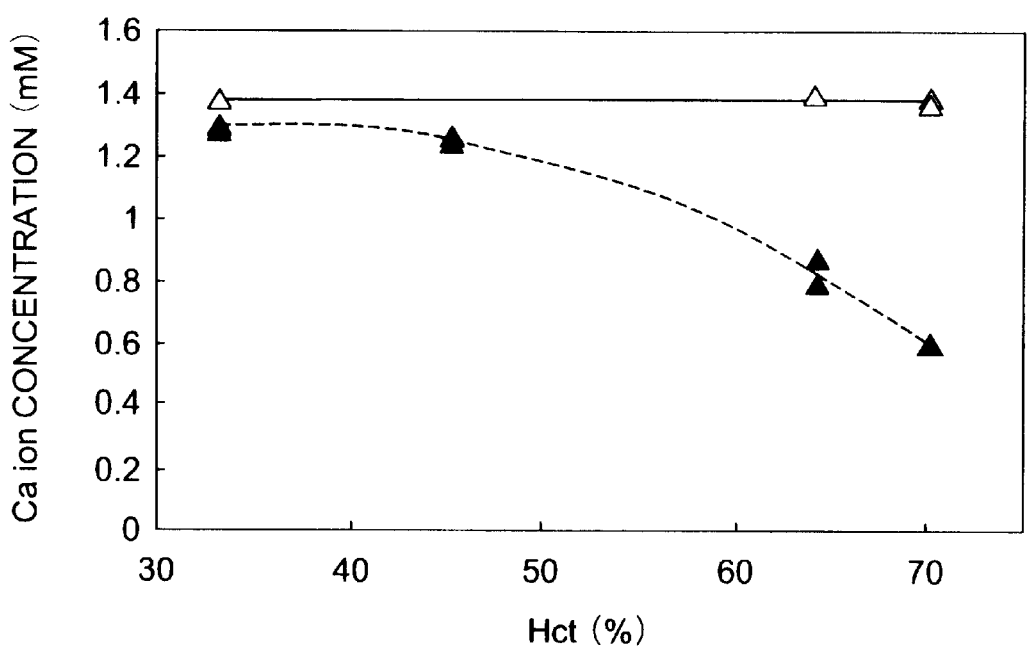
FIG. 4 is a graph illustrating the values of calcium ion concentration in a test liquid that have been measured using the multi-ion sensor plate of Example 2 of this invention in comparison with the values obtained from Comparative Example.

The solid line and the dotted line shown in FIG. 4 represent average values of two data on the value of Hct % in each sample.

EXAMPLE 6

0.8 mg of quarternary amine salt (supply source of Cl−) such as trioctylmethyl ammonium chloride was added to 2 g of DOA (dioctyl adipate) (plasticizer) to obtain a mixture, to which 10 mg of AgCl powder (electric potential-stabilizing agent) was added and stirred. Then, 250 mg of the supernatant of this mixture was taken up and mixed with 155 mg of PVC (a copolymer of; vinyl chloride:vinyl acetate:vinyl alcohol=90:4:6, which was available from Denki Kagaku Kogyo K.K.), with 14 mg of valinomycin (ionophore for detecting potassium ion), with 1.24 mg of K-TCPB (potassium tetrakis(p-chlorophenyl) borate; Dojin Kagaku Co., Ltd., anion scavenger), and with 250 mL of THF (tetrahydrofran) (solvent) to obtain a resinous solution for preparing an ion sensitive membrane.

Although the aforementioned supernatant contained quaternary amine salt and AgCl, it could be disregarded as the quantity thereof was minimal, thus making it possible to assume this supernatant as being 250 mg of a plasticizer, and to assume it as being about 60% by weight based on the non-volatile matters (ion sensitive membrane).

This resinous solution for forming an ion sensitive membrane was dripped onto the silver chloride layers 4a and 4b through the through-holes 6a and 6'a in the same manner as explained in Example 5, whereby forming coated layers which were then air-dried to form a potassium ion sensitive membrane functioning as an ion-sensitive film 2d.

A multi-ion sensor plate was prepared in the same manner as explained in Example 5 except that the aforementioned ion sensitive membrane was employed.

Figure 5:
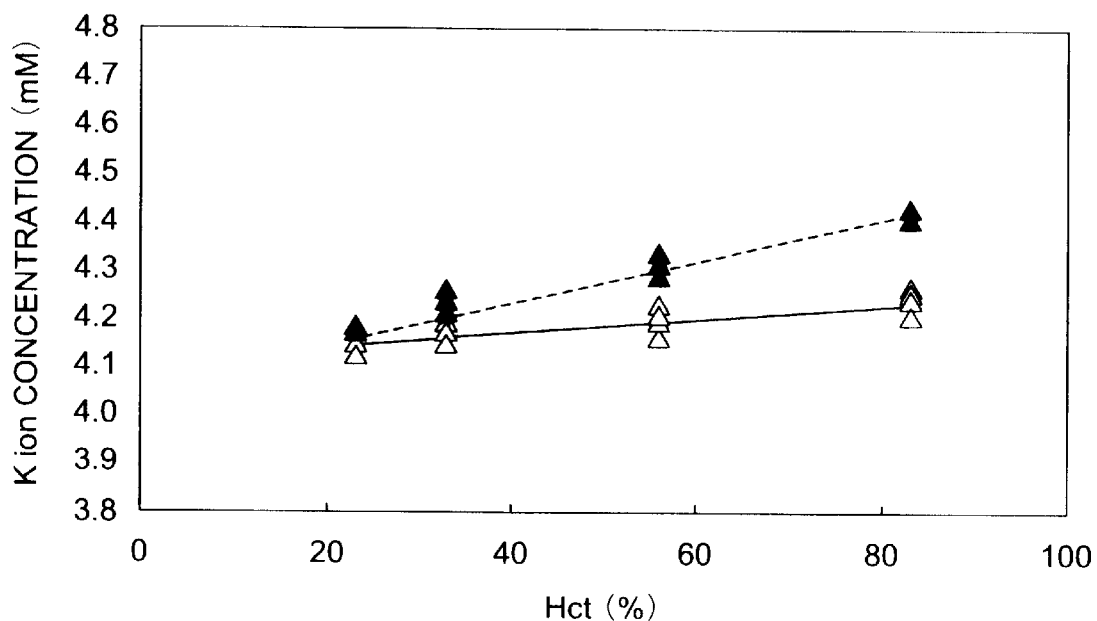
FIG. 5 is a graph illustrating the values of calcium ion concentration in a test liquid that have been measured using the multi-ion sensor plate of Example 3 of this invention in comparison with the values obtained from Comparative Example.

Then, by making use of this multi-ion sensor plate, the potassium ion concentration was measured to obtain the results shown in FIG. 5 by a solid line.

Comparative Example 3

As in the case of Comparative Example 2, potassium ion concentration was measured in the same manner as explained in Example 6, except that the surfactant was not coated on the inner surfaces of the passageways 13 and 14 of the upper cell 12, i.e. the conditions of the inner surfaces thereof were the same as those obtained immediately after the manufacture thereof. The results being shown in FIG. 5 by a dotted line.

EXAMPLE 7

0.8 mg of quarternary amine salt (supply source of Cl−) such as trioctylmethyl ammonium chloride was added to 2 g of NPOE (2-nitrophenyloctyl ether) (plasticizer) to obtain a mixture, to which 10 mg of AgCl powder (electric potential-stabilizing agent) was added and stirred. Then, 250 mg of the supernatant of this mixture was taken up and mixed with 190 mg of PVC (a copolymer of; vinyl chloride:vinyl acetate:vinyl alcohol=90:4:6, which was available from Denki Kagaku Kogyo K.K.), with 12.4 mg of Bis(12-crown-4) (ionophore for detecting sodium ion), with 0.86 mg of Na-TPB (sodium tetrakisphenyl) borate; Dojin Kagaku Co., Ltd., anion scavenger), and with 250 mL of THF (tetrahydrofran) (solvent) to obtain a resinous solution for preparing an ion sensitive membrane.

The ratio of NPOE in the non-volatile matters of the composition (excluding THF) employed for this ion sensitive membrane-forming resinous solution was 55% by weight.

This resinous solution for forming an ion sensitive membrane was dripped onto the silver chloride layers 4a and 4b through the through-holes 6a and 6'a in the same manner as explained in Example 1, whereby forming coated layers which were then air-dried to form a sodium ion sensitive membrane functioning as an ion-sensitive film 2d.

A multi-ion sensor plate was prepared in the same manner as explained in Example 5 except that the aforementioned ion sensitive membrane was employed. Then, by making use of this multi-ion sensor plate, the sodium ion concentration was measured to obtain the results shown in FIG. 6 by a solid line.

Comparative Example 4

As in the case of Comparative Example 2, sodium ion concentration was measured in the same manner as explained in Example 7, except that the surfactant was not coated on the inner surfaces of the passageways 13 and 14 of the upper cell 12, i.e. the conditions of the inner surfaces thereof were the same as those obtained immediately after the manufacture thereof. The results being shown in FIG. 6 by a dotted line.

Figure 6:
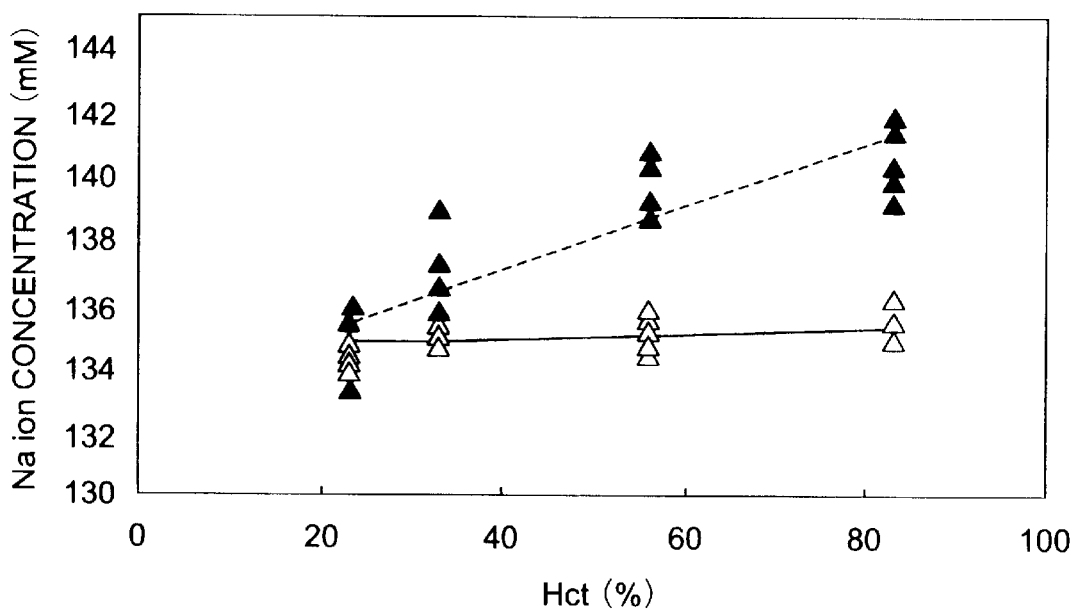
FIG. 6 is a graph illustrating the values of calcium ion concentration in a test liquid that have been measured using the multi-ion sensor plate of Example 4 of this invention in comparison with the values obtained from Comparative Example.

The solid line and the dotted line shown in FIGS. 5 and 6 represent average values of five data on the value of Hct % in each sample.

As seen from FIGS. 4 to 6, the multi-ion sensor plate where a surfactant was coated on the passageways of the upper cell indicated a constant ion concentration irrespective of the values of Hct %. Whereas, it the case of Comparative Example 2 shown in FIG. 4, calcium ion concentration was lowered approximately in proportion to an increase in value of Hct %. In the case of Comparative Examples shown in FIGS. 5 And 6 however, each ion concentration was increased in proportion to an increase in value of Hct %. These results demonstrate prominent effects that can be obtained by the employment of the surfactant according to these Examples.

It will be seen that in the case of FIG. 4, when the value of Hct % is not less than 40 to 45%, a difference in measured value starts to increase, while in the case of FIGS. 5 and 6, when the value of Hct% becomes higher than 20%, a difference in measured value starts to increase.

In view of these facts, if the ion concentration of each of potassium and sodium is to be detected according to the aforementioned items (6) and (15), it is desirable to employ a test liquid having an Hct % value of at least 40%. In the case of measuring calcium ion concentration, a test liquid indicating the Hct % value of at least 20% should be employed. It is generally preferable to employ a test liquid indicating the Hct % value of at least 20% or at least 40%.

EXAMPLE 8

0.8 mg of quarternary amine salt (supply source of Cl−) such as trioctylmethyl ammonium chloride was added to 2 g of DOA (dioctyl adipate) (plasticizer) to obtain a mixture, to which 10 mg of AgCl powder (electric potential-stabilizing agent) was added and stirred. Then, 250 mg of the supernatant of this mixture was taken up and mixed with 72 mg of PVC (a copolymer of; vinyl chloride:vinyl acetate:vinyl alcohol=90:4:6, which was available from Denki Kagaku Kogyo K.K.), with 14 mg of valinomycin (ionophore for detecting potassium ion), with 1.24 mg of K-TCPB (potassium tetrakis(p-chlorophenyl) borate; Dojin Kagaku Co., Ltd., anion scavenger), and with 250 mL of THF (tetrahydrofran) (solvent) to obtain a resinous solution for preparing an ion sensitive membrane.

Figure 7:
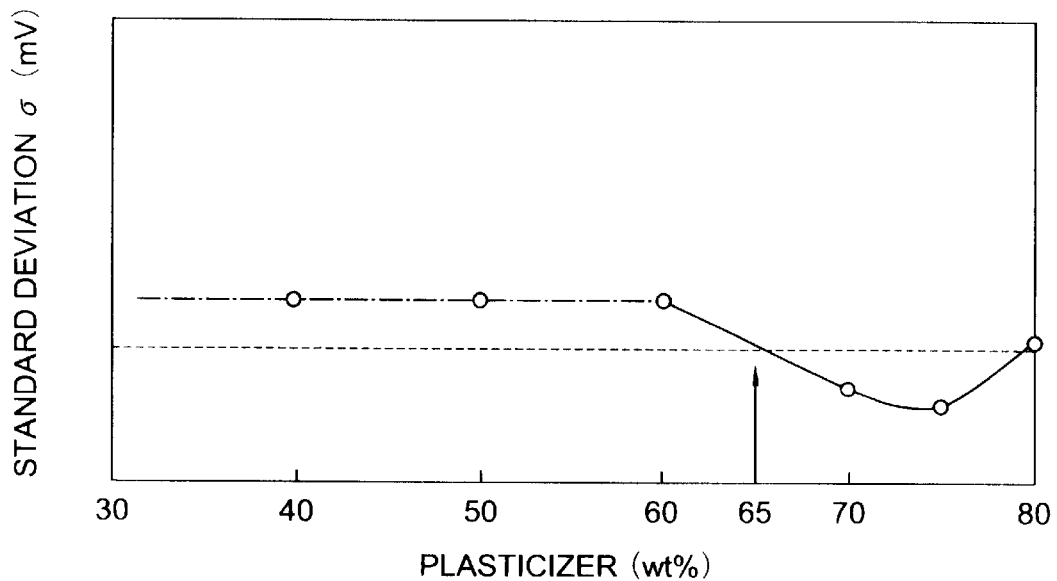
FIG. 7 is a graph illustrating the relationship between the standard deviation of electric potential corresponding to the potassium ion concentration and the weight (%) of a plasticizer that has been obtained using the multi-ion sensor plate of Example 5 of this invention.

The composition of non-volatile matter of this ion sensitive membrane-forming resinous solution (excluding THF) and the ratio (75% by weight) of DOA in the non-volatile containing 40% by weight, 50% by weight or 60% by weight of a plasticizer, were manufactured in the same manner as explained in Example 8 except that the quantity of PVC employed was 350 mg, 235 mg or 155 mg. Thereafter, the electric potential of each multi-ion sensor plate was measured in the same manner as explained in Example 8. Then, standard deviation was also calculated from these measured values as shown in FIG. 7.

TABLE 2

|  | EX. 8 | EX. 9 | EX. 10 | COMP. EX. 5 | COMP. EX. 6 | COMP. EX. 7 |
| --- | --- | --- | --- | --- | --- | --- |
| PLASTICIZER (wt %) | 75 | 70 | 80 | 40 | 50 | 60 |
| PVC (mg) (RESIN) | 72 | 95 | 50 | 350 | 235 | 155 |
| DOA (mg) (PLASTICIZER) | 250 | 250 | 250 | 250 | 250 | 250 |
| VALINOMYCIN (IONOPHORE) | 14 | 14 | 14 | 14 | 14 | 14 |
| K-TCPB (mg) (ANION SCAVENGER) | 1.24 | 1.24 | 1.24 | 1.24 | 1.24 | 1.24 |

DOA (mg) DENOTES THE WEIGHT OF SUPERNATANT OF MIXTURE OF Agcl, QUATERNARY AMINE SALT AND DOA.

matters are shown in Table 2. By the way, although the aforementioned supernatant contained quaternary amine salt and AgCl, it could be disregarded as the quantity thereof was minimal, thus making it possible to assume this supernatant as being about 75% by weight based on the non-volatile matters (the same with other composition).

This resinous solution for forming an ion sensitive membrane was dripped onto the silver chloride layers 4a and 4b through the through-holes 6a and 6'a in the same manner as explained in Example 1, whereby forming coated layers which were then air-dried to form a potassium ion sensitive membrane functioning as an ion-sensitive film 2d.

The multi-ion sensor plate having a structure shown in FIGS. 1 and 2 was prepared in total of 20 pieces. Then, by making use of the multi-ion sensor plates immediately after the manufacture thereof, the electric potential of each sample sensor plate was measured according to the aforementioned measuring method using an aqueous solution containing 4 mM KCl as a test liquid, and a prescribed reference liquid as a reference liquid. Subsequently, the standard deviation (σ(mV)) was calculated, the results being shown in FIG. 7.

By the way, the actual value of potassium ion concentration was obtained by applying the measured value of electric potential to the relationship between the electric potential and the concentration that had been prepared in advance (the same hereinafter).

EXAMPLES 9 AND 10

Multi-ion sensor plates of Examples 9 and 10, each provided with a potassium ion sensitive membrane containing 70% by weight or 80% by weight of a plasticizer, were manufactured in the same manner as explained in Example 8 except that the quantity of PVC employed was 95 mg or 50 mg. Thereafter, the electric potential of each multi-ion sensor plate was measured in the same manner as in the case of Example 8. Then, standard deviation was also calculated from these measured values as shown in FIG. 7.

Comparative Examples 5 to 7

Multi-ion sensor plates of Comparative Examples 5 to 7, each provided with a potassium ion sensitive membrane

EXAMPLE 11

0.86 mg of quarternary amine salt (supply source of Cl−) such as trioctylmethyl ammonium chloride was added to 2 g of NPOE (2-nitrophenyloctyl ether) (plasticizer) to obtain a mixture, to which 10 mg of AgCl powder (electric potential-stabilizing agent) was added and stirred. Then, 250 mg of the supernatant of this mixture was taken up and mixed with 72 mg of PVC (a copolymer of; vinyl chloride:vinyl acetate:vinyl alcohol=90:4:6, which was available from Denki Kagaku Kogyo K.K.), with 14 mg of valinomycin (ionophore for detecting potassium ion), with 12.4 mg of Bis(12-crown-4) (ionophore for detecting sodium ion), with 12.4 mg of Na-TPB (sodium tetrakisphenyl) borate; Dojin Kagaku Co., Ltd., anion scavenger), and with 250 mL of THF (tetrahydrofran) (solvent) to obtain a resinous solution for preparing an ion sensitive membrane.

The composition of non-volatile matter of this ion sensitive membrane-forming resinous solution (excluding THF) and the ratio (75% by weight) of NPOE in the non-volatile matters are shown in Table 3. By the way, the calculation of the quantity of the plasticizer (250 mg) and the weight % thereof were performed in the same manner as illustrated with reference to those of Table 2.

This resinous solution for forming an ion sensitive membrane was dripped onto the silver chloride layers 4a and 4b through the through-holes 6a and 6'a in the same manner as explained in Example 8, whereby forming coated layers which were then air-dried to form a sodium ion sensitive membrane functioning as an ion-sensitive film 2d.

By making use of the sodium ion-sensitive film, multi-ion sensor plates were prepared in total of 20 pieces. Then, by making use of the multi-ion sensor plates immediately after the manufacture thereof, the electric potential of each sample sensor plate was measured according to the aforementioned measuring method using an aqueous solution containing 140 mM NaCl as a test liquid, and a prescribed reference liquid as a reference liquid. Subsequently, the standard deviation (σ(mV)) was calculated, the results being shown in FIG. 8.

EXAMPLES 12 AND 13

Figure 8:
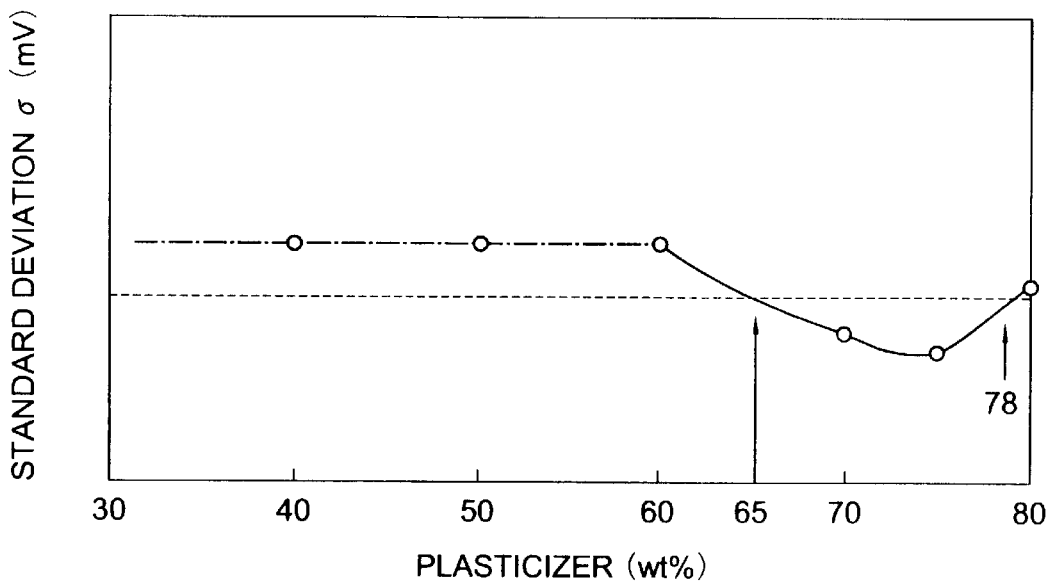
FIG. 8 is a graph illustrating the relationship between the standard deviation of electric potential corresponding to the sodium ion concentration and the weight (%) of a plasticizer that has been obtained using the multi-ion sensor plate of Example 6 of this invention.

Multi-ion sensor plates of Examples 12 and 13, each provided with a potassium ion sensitive membrane containing 70% by weight or 80% by weight of a plasticizer, were manufactured in the same manner as explained in Example 11 except that the quantity of PVC employed was 95 mg or 50 mg. Thereafter, the electric potential of each multi-ion sensor plate was measured in the same manner as in the case of Example 8. Then, standard deviation was also calculated from these measured values as shown in FIG. 8.

Comparative Examples 8 to 10

Multi-ion sensor plates of Comparative Examples 8 to 10, each provided with a potassium ion sensitive membrane containing 40% by weight, 50% by weight or 60% by weight of a plasticizer, were manufactured in the same manner as explained in Example 11 except that the quantity of PVC employed was 350 mg, 235 mg or 155 mg. Thereafter, the electric potential of each multi-ion sensor plate was measured in the same manner as in the case of Example 8. Then, standard deviation was also calculated from these measured values as shown in FIG. 8.

cathode, an anodic oxidation treatment was performed in a hydrochloric acid solution at an anode current density of 0.23 A/dm$^2$ for 2 minutes 40 seconds, thereby forming a silver chloride layer which was composed of silver chloride particles each having a diameter of about 1 $\mu$m (the value as measured by means of scanning electron microscope). Then, ultraviolet rays (intensity: 70 mW/cm$^2$) was applied for 150 seconds to this silver chloride layer by making use of a high-pressure mercury lamp, thereby forming the modified silver chloride layer 4a.

Figure 9:
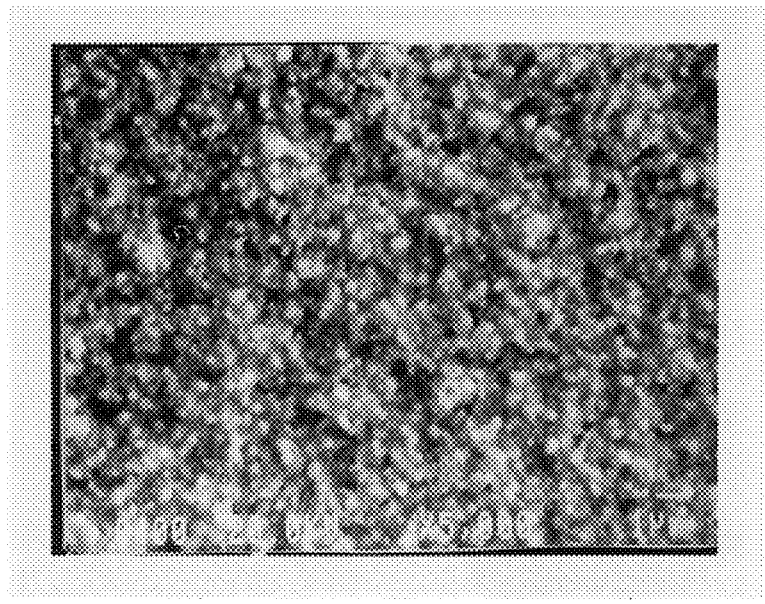
FIG. 9 is an electron microscopic photograph illustrating a modified silver chloride layer of the electrode of the multi-ion sensor plate of Example 7 of this invention.
Figure 12:
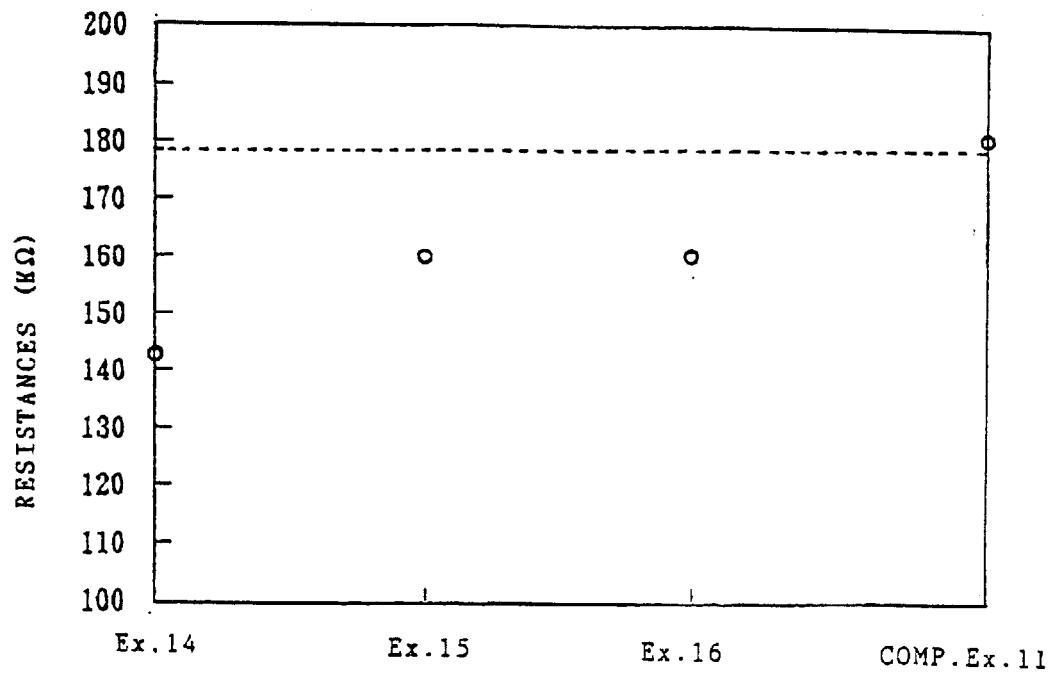
FIG. 12 is a graph illustrating the electric resistances of a modified silver chloride layer and of a silver chloride layer that have been obtained using the multi-ion sensor plate of Example 9 of this invention and the multi-ion sensor plate of Comparative Example.

FIG. 9 illustrates a photograph which was taken by using the scanning electron microscope after the irradiation of ultraviolet rays. The particle diameter of the silver chloride layer after the irradiation of ultraviolet rays was in the range of 0.2 $\mu$m to 0.7 $\mu$m. Further, when the atomic ratio of Ag/Cl of the silver chloride layer after the irradiation of ultraviolet rays was analyzed by making use of EDS (an energy dispersive element detector), the results shown in Table 4 were obtained. FIG. 12 shows the values of resistance measured on the modified silver chloride layer after the

TABLE 3

|  | EX. 11 | EX. 12 | EX. 13 | COMP. EX. 8 | COMP. EX. 9 | COMP. EX. 10 |
|---|---|---|---|---|---|---|
| PLASTICIZER (wt %) | 75 | 70 | 80 | 40 | 50 | 60 |
| PVC (mg) (RESIN) | 72 | 95 | 50 | 350 | 235 | 155 |
| NPOE (mg) (PLASTICIZER) | 250 | 250 | 250 | 250 | 250 | 250 |
| BIS (12-CROWN-4) (mg) (IONOPHORE) | 12.4 | 12.4 | 12.4 | 12.4 | 12.4 | 12.4 |
| Na-TPB (mg) (ANION SCAVENGER) | 0.86 | 0.86 | 0.86 | 0.86 | 0.86 | 0.86 |

NPOE (mg) DENOTES THE WEIGHT OF SUPERNATANT OF MIXTURE OF Agcl, QUATERNARY AMINE SALT AND NPOE.

In FIGS. 7 and 8, the dotted line denotes a modified reference line; the solid line denotes a sequence of values of the standard deviation ($\sigma$(mV)) which are linked with each other and obtained from the above Comparative Examples 7 and 10 where the quantity of the plasticizer is 60% by weight and from Example where the quantity of the plasticizer is 65% by weight or more; and the dot and dash line denotes a sequence of values of the standard deviation ($\sigma$(mV)) which are linked with each other and obtained from the above Comparative Examples where the quantity of the plasticizer is less than 60% by weight. If the value of the standard deviation ($\sigma$(mV)) is lower in relative the modified reference line, it indicates an improvement in performance of the sensor.

As seen from FIGS. 7 and 8, when the quantity of the plasticizer is in the range of 65% by weight to 80% by weight, the performance of the sensor was improved. When the quantity of the plasticizer is in the range of 65% by weight to 78% by weight, the solid line is located lower than the modified reference line in FIG. 8, so that this range is more preferable not only in the case of FIG. 8 but also the case of FIG. 7. Most preferable range in quantity of the plasticizer is in the range of 70% by weight to 75% by weight in both FIGS. 7 and 8.

EXAMPLE 14

The electrode of the multi-ion sensor plate main body 5 shown in FIG. 2 will be explained with reference to FIG. 1 or the electrode which is disposed on the side where a test liquid is supplied. As mentioned above, a silver plating was performed on the copper foil of the test liquid-measuring electrode 2a. Then, while employing this Ag-plated electrode as an anode, and a platinum-plated titanium mesh as a irradiation of ultraviolet rays. By the way, the dotted line therein is a modified reference line.

TABLE 4

|  | EX. 14 (ULTRA-VIOLET RAYS: INTENSITY; 70 mW/cm$^2$) | EX. 15 (ULTRA-VIOLET RAYS: INTENSITY; 70 mW/cm$^2$) | EX. 16 (ETCHING UNDER NATURAL LIGHT) | COMP. EX. (REDUCTION NOT PERFORMED) |
|---|---|---|---|---|
| Ag/Cl RATIO | 1.67 | 1.30 | 1.26 | 1.09 |

The electrode to be disposed on the test liquid-supplying side could be prepared in this manner. Accordingly, the other electrode to be disposed on the reference liquid-supplying side and to be paired with the aforementioned electrode was also prepared in the same manner as mentioned above, and then, other pairs of electrodes were prepared in the same manner as mentioned above. Thereafter, the multi-ion sensor plate main body 5 and channel body 9 was bonded together as shown in FIG. 2 to obtain a combined body.

Next, an ion sensitive membrane for each electrode was formed as follow.

0.8 mg of quarternary amine salt (supply source of Cl–) such as trioctylmethyl ammonium chloride was added to 2 g of DOA (dioctyl adipate) (plasticizer) to obtain a mixture, to which 10 mg of AgCl powder (electric potential-stabilizing agent) was added and stirred. Then, 250 mg of the supernatant of this mixture was taken up and mixed with 72 mg of PVC (a copolymer of; vinyl chloride:vinyl acetate:vinyl alcohol=90:4:6, which was available from Denki Kagaku Kogyo K.K.), with 14 mg of valinomycin (ionophore for detecting potassium ion), with 1.24 mg of K-TCPB (potassium tetrakis(p-chlorophenyl) borate; Dojin Kagaku Co., Ltd., anion scavenger), and with 250 mL of THF (tetrahydrofran) (solvent) to obtain a resinous solution for preparing an ion sensitive membrane.

The ratio of DOA in the non-volatile matters of the composition (excluding THF) employed for this ion sensitive membrane-forming resinous solution could be approximated as being 75% by weight.

This resinous solution for forming an ion sensitive membrane was dripped onto the silver chloride layers 4a and 4b through the through-holes 6a and 6'a in the same manner as explained in Example 1, whereby forming coated layers which were then air-dried to form a potassium ion sensitive membrane functioning as an ion-sensitive film 2d.

The multi-ion sensor plate having a structure shown in FIGS. 1 and 2 was prepared in total of 20 pieces. Then, by making use of the multi-ion sensor plates immediately after the manufacture thereof, the electric potential of each sample sensor plate was measured according to the aforementioned measuring method using an aqueous solution containing 4 mM KCl as a test liquid, and a prescribed reference liquid as a reference liquid. Subsequently, the standard deviation (σ(mV)) was calculated, the results being shown in FIG. 7.

By the way, the actual value of potassium ion concentration was obtained by applying the measured value of electric potential to the relationship between the electric potential and the concentration that had been prepared in advance (the same hereinafter).

EXAMPLE 15

Figure 13:
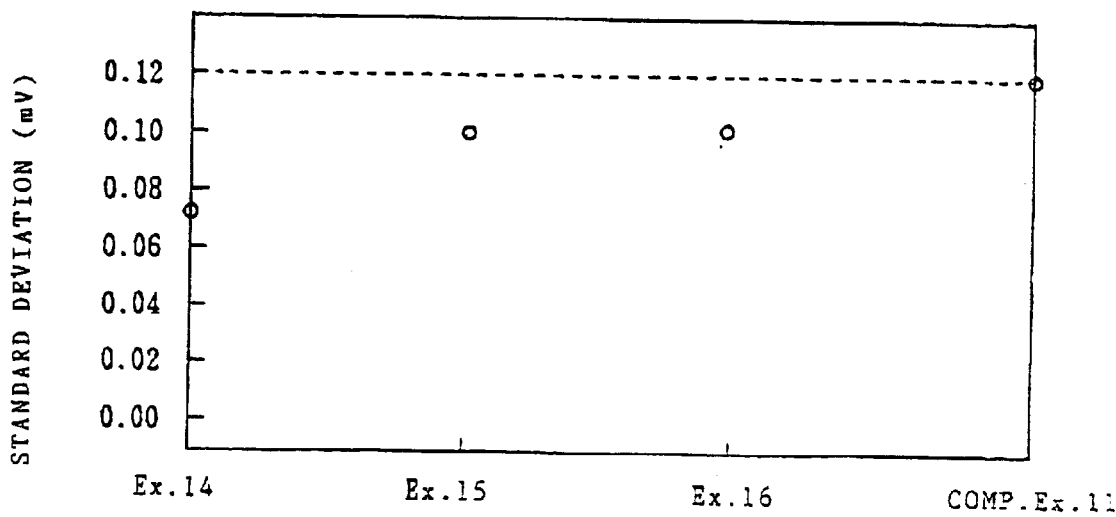
FIG. 13 is a graph illustrating the standard deviations of measured values of electric potential of electrode that have been obtained using the multi-ion sensor plate of Example 9 of this invention and the multi-ion sensor plate of Comparative Example.

The same procedures as explained in Example 14 were repeated except that the irradiation of the ultraviolet rays was performed under the conditions of: 70 mW/cm$^2$ and 30 seconds, thereby obtaining the Ag/Cl ratio of the modified silver chloride layer and the values of electric resistance, the results being shown in Table 4 and FIG. 12, respectively. Further, in the same manner as illustrated in Example 1 except that the silver chloride layer was prepared as mentioned above, the multi-ion sensor plates were prepared in total of 20 pieces. Thereafter, the electric potential of each multi-ion sensor plate was measured in the same manner as in the case of Example 1, and then, the standard deviation thereof was calculated from these measured values as shown in FIG. 13.

EXAMPLE 16

Figure 10:
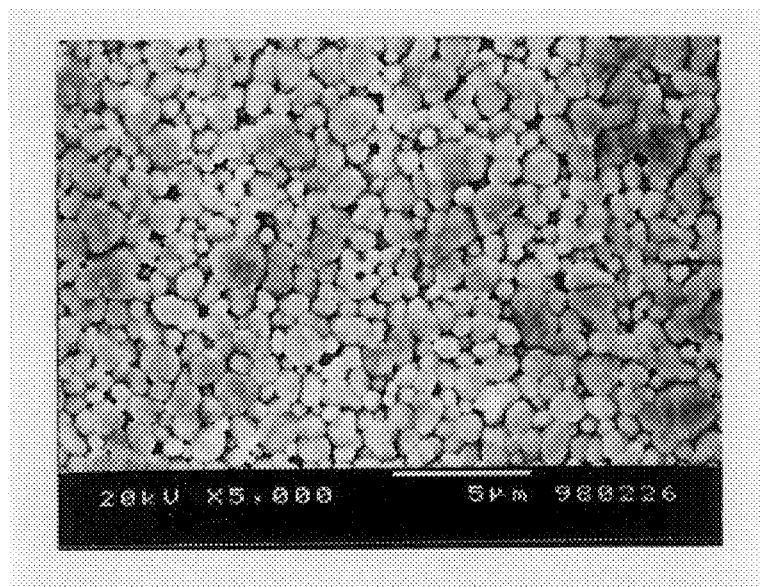
FIG. 10 is an electron microscopic photograph illustrating a modified silver chloride layer of the electrode of the multi-ion sensor plate of Example 8 of this invention.

The same procedures as explained in Example 14 were repeated wherein the silver chloride layer was immersed for 5 hours in a solution containing chlorine ion at a concentration of 10 mM (trioctylmethyl ammonium chloride) thereby slightly dissolving (etching) the grain boundary of the silver chloride. This procedures were performed under sun light thereby to form a modified silver chloride layer. The photograph showing this particle size which was taken by means of scanning electron microscope is shown in FIG. 10. The particle diameter of the particles of this modified silver chloride layer after this etching treatment was in the range of 0.4 to 0.8 μm. Further, the atomic ratio of Ag/Cl of the silver chloride layer was analyzed in the same manner as in Example 14, the results being shown in Table 4. FIG. 12 shows the values of resistance measured on the modified silver chloride layer.

20 pieces of the multi-ion sensor plates, each provided with a potassium ion sensitive membrane which was prepared in the same manner as in Example 1 except that the modified silver chloride layer was obtained as mentioned above, were prepared. Then, the electric potential of these sensor plates was measured in the same manner as in Example 1, and the standard deviation (σ(mV)) thereof was calculated, the results being shown in FIG. 13.

Comparative Example 11

Figure 11:
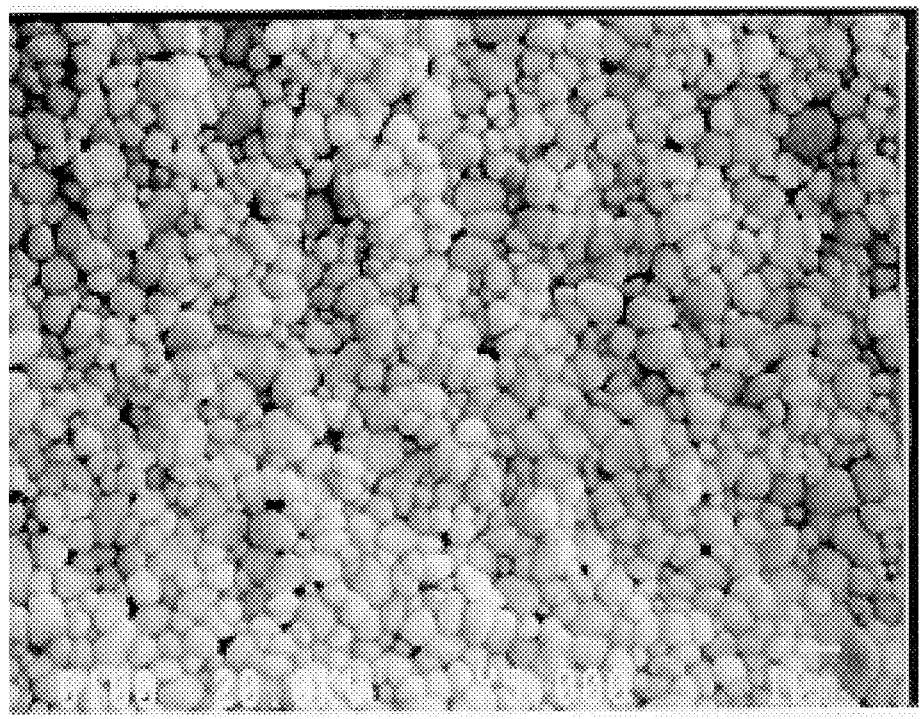
FIG. 11 is an electron microscopic photograph of a modified silver chloride layer of the electrode of the multi-ion sensor plate of Comparative Example.

The same procedures as explained in Example 14 were repeated except that the irradiation of ultraviolet rays was omitted and the subsequent procedures were performed under sun light thereby to form the electrodes. The photograph showing this particle size which was taken by means of scanning electron microscope is shown in FIG. 11. The particle diameter of the particles of this silver chloride layer was about 1 μm. Further, the atomic ratio of Ag/Cl of the silver chloride layer was analyzed, the results being shown in Table 4. FIG. 12 shows the values of resistance measured on the silver chloride layer.

20 pieces of the multi-ion sensor plates, each provided with a potassium ion sensitive membrane which was prepared in the same manner as in Example 1 except that the electrodes were formed as mentioned above, were prepared. Then, the electric potential of these sensor plates was measured in the a same manner as in Example 1, and the standard deviation thereof was calculated, the results being shown in FIG. 13.

As seen from these results, Example 14 indicated most preferable results in all aspects of measurement. The results obtained by Example 15 were superior than those of Example 16. However the results obtained in Example 16 were superior than those of Comparative Example 11, thus indicating that the larger the effect of the irradiation of ultraviolet rays was, the more excellent in performance thereof.

According to this invention, the particle diameter of the modified silver chloride layer may be in the range of 0.2 μm to 0.7 μm, 0.2 μm to 0.8 μm, 0.4 μm to 0.7 μm, or 0.4 μm to 0.8 μm. Further, the Ag/X ratio may be in the range of 1.2 to 1.6, 1.3 to 1.6, or more than 1.6 (in the presence of silver halide layer).

The modification of the silver halide layer can be performed by means of reduction. The reduction is performed for the purpose of increasing the ratio of silver in the silver halide layer (AgX). Therefore, any means which is capable of reducing silver ion into silver can be employed. Specifically, a physical reduction means employing ultraviolet rays or a beam including ultraviolet rays (a beam mainly including ultraviolet rays or the natural light), or a chemical reduction means employing a reducing agent can be employed.

When an etching that can be performed under a light mainly including ultraviolet rays or under sun light is employed, the reduction treatment can be performed easily and readily. In particular, since any chemicals are required to be employed if only light is employed in this treatment, a modified silver halide layer which is free from any impurities, low in resistance and minimal in consistency of performance would be obtained.

When the etching (wherein the modification of the silver halide is effected by the dissolution of the grain boundary) is performed using a solution containing a halogen (a non-aqueous chloride solution such as an alcoholic solution of an organic chloride which is capable of supplying a halogen ion may be suited for moderately performing the etching thus enabling an easy control of the etching degree, but other chloride solution can be also employed), an halogen ion and a complex $AgX_2^-$ will be generated from the silver halide, thereby dissolving the grain boundary, erasing the crystal and minimizing the grain diameter. As a result, the underlying silver layer may be exposed from the grain boundary thus dissolved, and hence the Ag/Cl ratio can be increased in the reducing treatment.

When the grain size of the silver halide of the modified silver halide layer is minimized this manner, the contacting area thereof with the ion sensitive membrane would be increased, and at the same time, the ratio of silver in the silver halide layer would be increased, thus improving the conductivity of the silver halide layer containing silver halide which is inherently insulative.

According to this invention, an electric potential-stabilizing agent or a material pertinent to the electric potential-stabilizing agent is incorporated into an ion sensitive membrane for the purpose of minimizing the electric resistance of the modified silver halide layer, and at the same time, for the purpose of suitably inhibiting the constituent materials for the dissociation equilibrium of AgX ($AgX \leftrightarrows Ag^+ + X^-$) from being dissolved into the ion sensitive membrane, thus stabilizing (fixing) the dissociation equilibrium. As a result, the stabilization of the electric potential at the interface between the modified silver halide layer and the ion sensitive membrane can be readily performed, thus making it possible to minimize any inconsistency in electric potential, to keep an excellent measurement precision not only immediately after the manufacture thereof but also after a lapse of time, and to save the manufacturing cost.

According to this invention, since an electric potential-stabilizing agent or a material pertinent to the electric potential-stabilizing agent is incorporated into an ion sensitive membrane, it has become possible to provide an ion sensor and an ion sensor plate, which are excellent in initial characteristics immediately after the manufacture thereof, minimal in inconsistency in characteristics, capable of saving the time for carrying out the correction of the initial characteristics or the stabilization of the characteristics, and capable of exhibiting a high precision measuring value not only immediately after the manufacture thereof, but also after a lapse of time, thus making it possible to save the manufacturing cost.

According to this invention, since at least the test liquid contains a surfactant to such an extent that it can be supplied to the test liquid-measuring electrode, it becomes possible to provide an ion sensor and an ion sensor plate, which are simple in structure, excellent in productivity, capable of maintaining the dispersion stability of submerged and dispersed substances such as hemocyte or protein reflecting the hematocrit in a test liquid to be supplied to the measuring electrode of the test liquid at the occasion of measurement so as to prevent the dispersed substances from being settled on the test liquid-measuring electrode at the occasion of measurement. As a result, it is possible to provide an ion sensor and an ion sensor plate, which are capable of not indicating an abnormal value in the measurement of ion concentration, thus making it possible to measure the ion concentration with high precision.

According to this invention, since a plasticizer is incorporated into the ion sensitive membrane at a ratio of 65 to 80% by weight, it is possible to provide an ion sensor and an ion sensor plate provided with an ion sensitive membrane which is uniform in composition and large in contact area with an underlying layer thereof, which is capable of enabling the effect of a potential-stabilizing agent or ionophore incorporated in the ion sensitive membrane to be effectively manifested. Additionally, it is possible to provide an ion sensor and an ion sensor plate, which are excellent in the initial characteristics immediately after the manufacture thereof, minimal in inconsistency of characteristics and hence excellent in precision of measurement and in reliability, and excellent in productivity. Therefore, this invention is applicable to a disposable simple-structured ion sensor and a disposable simple-structured ion sensor plate, which are capable of minimizing any bad influence even if a plasticizer, etc. is dissolved in a test liquid or a reference liquid.

Further, according to this invention, since the Ag/Cl ratio of the modified silver halide layer is selected to be at least 1.2, it is now possible to minimize the electric resistance of the modified silver halide layer. Furthermore, since the particle diameter of the modified silver halide layer is controlled to 1 μm or less, the contacting area thereof with the ion sensitive membrane can be increased, thus making it possible to minimize the electric resistance at the interface between the silver halide layer and the ion sensitive membrane. As a result, it is possible to minimize any influence that might be brought about by the ion to be generated by a current flowing through a measuring circuit or by the electric potential at this interface, thus making it possible to minimize the noise originating from the inconsistency of electric potential at the interface and to obtain an ion sensor and an ion sensor plate which are excellent in precision of the detected value of ion concentration.

The invention set forth hereinabove can be applied to various kinds of ion sensor and electrode cell. For example, the invention set forth hereinabove can be applied to a flow-type ion sensor comprising; at least one measuring electrode cell provided with a test liquid-feeding passageway and with a measuring electrode placed enabling a test liquid passing through said test liquid-feeding passageway to be contacted with the measuring electrode through an ion sensitive membrane sensitive to a specific ion; and a reference electrode cell provided with a test liquid-feeding passageway and with a reference electrode placed enabling a test liquid passing through said test liquid-feeding passageway to be contacted with the reference electrode through a reference liquid-measuring membrane; said measuring electrode cell and said reference electrode cell being communicated with each other through said passageway provided in each of them, thereby enabling to measure a potential difference between said reference electrode and said measuring electrode while allowing a test liquid to pass through said test liquid-feeding passageway communicating said measuring electrode cell with said reference electrode cell; wherein said flow-type ion sensor is characterized in that at least said measuring electrode cell among said measuring electrode cell and said reference electrode cell is constructed such that the measuring electrode thereof is formed of a silver chloride/silver electrode, i.e. a laminated structure consisting of an upper silver chloride layer and a lower silver layer; and in that said ion sensitive membrane is adhered onto said upper silver chloride layer of said silver chloride/silver electrode.

What is claimed is:

1. An ion sensor comprising:
an ion sensor plate main body provided with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer; and a measuring circuit connected with said ion sensor plate main body for measuring a concentration of said specific ion in said test liquid, wherein said ion sensitive membrane contains an electric potential-stabilizing agent which is capable of stabilizing an electric potential at an interface between said silver halide layer and said ion sensitive membrane, and the ion sensor being further provided with a test liquid-feeding passageway for supplying said test liquid to said test liquid-measuring electrode and with a reference liquid-feeding passageway for supplying said reference liquid to said reference electrode, wherein at least said test liquid-feeding passageway among these passageways is provided with a coated film of surfactant which is capable of adding said surfactant to said test liquid as said test liquid passes through said test liquid-feeding passageway.

2. An ion sensor comprising:

an ion sensor plate main body provided with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer; and a measuring circuit connected with said ion sensor plate main body for measuring a concentration of said specific ion in said test liquid, wherein said ion sensitive membrane contains an electric potential-stabilizing agent which is capable of stabilizing an electric potential at an interface between said silver halide layer and said ion sensitive membrane, wherein said silver halide layer formed on said silver layer is a modified silver halide layer which is modified in such a manner that the atomic ratio of silver and halogen: Ag/Cl is at least 1.2.

3. An ion sensor plate comprising:

an ion sensor plate main body having a substrate and provided on the substrate with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer;

an upper cell which is designed to form a closed channel for supplying a test liquid to said test liquid-measuring electrode and a closed channel for supplying a reference liquid to said reference electrode, and is provided with a test liquid inlet portion communicating with said closed channel for supplying said test liquid and with a reference liquid inlet portion communicating with said closed channel for supplying said reference liquid; and a liquid junction portion which is formed in said ion sensor plate main body and designed to allow said test liquid and said reference liquid supplied through said channels respectively to be contacted with each other, wherein said ion sensitive membrane contains an electric potential-stabilizing agent which is capable of stabilizing an electric potential at an interface between said silver halide layer and said ion sensitive membrane, wherein at least part of said closed channel for supplying said test liquid among these closed channels for supplying said test liquid and said reference liquid is provided with a coated film of surfactant which is capable of adding said surfactant to said test liquid as said test liquid passes through said closed channel for supplying said test liquid.

4. An ion sensor plate comprising:

an ion sensor plate main body having a substrate and provided on the substrate with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer;

an upper cell which is designed to form a closed channel for supplying a test liquid to said test liquid-measuring electrode and a closed channel for supplying a reference liquid to said reference electrode, and is provided with a test liquid inlet portion communicating with said closed channel for supplying said test liquid and with a reference liquid inlet portion communicating with said closed channel for supplying said reference liquid; and a liquid junction portion which is formed in said ion sensor plate main body and designed to allow said test liquid and said reference liquid supplied through said channels respectively to be contacted with each other, wherein said ion sensitive membrane contains an electric potential-stabilizing agent which is capable of stabilizing an electric potential at an interface between said silver halide layer and said ion sensitive membrane, wherein said silver halide layer formed on said silver layer is a modified silver halide layer which is modified in such a manner that the atomic ratio of silver and halogen: Ag/Cl is at least 1.2.

5. An ion sensor comprising:

an ion sensor plate main body provided with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer; and a measuring circuit connected with said ion sensor plate main body for measuring a concentration of said specific ion in said test liquid, wherein said ion sensitive membrane contains an electric potential-stabilizing agent which is capable of stabilizing an electric potential at an interface between said silver halide layer and said ion sensitive membrane, wherein said electric potential-stabilizing agent is composed of a halogen ion and/or silver ion, or a compound which is capable of dissociating a halogen ion and/or silver ion, and the ion sensor being further provided with a test liquid-feeding passageway for supplying said test liquid to said test liquid-measuring electrode and with a reference liquid-feeding passageway for supplying said reference liquid to said reference electrode, wherein at least said test liquid-feeding passageway among these passageways is provided with a coated film of surfactant which is capable of adding said surfactant to said test liquid as said test liquid passes through said test liquid-feeding passageway.

6. An ion sensor comprising:

an ion sensor plate main body provided with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer; and a measuring circuit connected with said ion sensor plate main body for measuring a concentration of said specific ion in said test liquid, wherein said ion sensitive membrane contains an electric potential-stabilizing agent which is capable of stabilizing an electric potential at an interface between said silver halide layer and said ion sensitive membrane, wherein said electric potential-stabilizing agent is composed of a halogen ion and/or silver ion, or a compound which is capable of dissociating a halogen ion and/or silver ion, wherein said silver halide layer formed on said silver layer is a modified silver halide layer which is modified in such a manner that the atomic ratio of silver and halogen: Ag/Cl is at least 1.2.

7. An ion sensor plate comprising:

an ion sensor plate main body having a substrate and provided on the substrate with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer;

an upper cell which is designed to form a closed channel for supplying a test liquid to said test liquid-measuring electrode and a closed channel for supplying a reference liquid to said reference electrode, and is provided with a test liquid inlet portion communicating with said closed channel for supplying said test liquid and with a reference liquid inlet portion communicating with said closed channel for supplying said reference liquid; and a liquid junction portion which is formed in said ion sensor plate main body and designed to allow said test liquid and said reference liquid supplied through said channels respectively to be contacted with each other, wherein said ion sensitive membrane contains an electric potential-stabilizing agent which is capable of stabilizing an electric potential at an interface between said silver halide layer and said ion sensitive membrane, wherein said electric potential-stabilizing agent is composed of a halogen ion and/or silver ion, or a compound which is capable of dissociating a halogen ion and/or silver ion, wherein at least part of said closed channel for supplying said test liquid among these closed channels for supplying said test liquid and said reference liquid is provided with a coated film of surfactant which is capable of adding said surfactant to said test liquid as said test liquid passes through said closed channel for supplying said test liquid.

8. An ion sensor plate comprising:

an ion sensor plate main body having a substrate and provided on the substrate with at least one group of an electrode pair, each group having a test liquid-measuring electrode and a reference electrode, each of the test liquid electrode and the reference electrode being provided with a silver halide layer formed on a silver layer and with an ion sensitive membrane which is sensitive to a specific ion and formed on said silver halide layer;

an upper cell which is designed to form a closed channel for supplying a test liquid to said test liquid-measuring electrode and a closed channel for supplying a reference liquid to said reference electrode, and is provided with a test liquid inlet portion communicating with said closed channel for supplying said test liquid and with a reference liquid inlet portion communicating with said closed channel for supplying said reference liquid; and a liquid junction portion which is formed in said ion sensor plate main body and designed to allow said test liquid and said reference liquid supplied through said channels respectively to be contacted with each other, wherein said ion sensitive membrane contains an electric potential-stabilizing agent which is capable of stabilizing an electric potential at an interface between said silver halide layer and said ion sensitive membrane, wherein said electric potential-stabilizing agent is composed of a halogen ion and/or silver ion, or a compound which is capable of dissociating a halogen ion and/or silver ion, wherein said silver halide layer formed on said silver layer is a modified silver halide layer which is modified in such a manner that the atomic ratio of silver and halogen: Ag/Cl is at least 1.2.

9. The ion sensor according to claim 1, 2, 5 or 6, wherein said electric potential-stabilizing agent is silver chloride.

10. The ion sensor according to claim 1, 2, 5 or 6, wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an ion sensitive material which is higher than that is required for responding to said specific ion.

11. The ion sensor according to claim 1, 2, 5 or 6, wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an electric potential-stabilizing agent which is higher than that is required for eliminating said disturbance by said anion.

12. The ion sensor according to claim 1, 2, 5 or 6, wherein said ion sensitive membrane contains at least a matrix, a plasticizer for plasticizing said matrix and an ion sensitive material, the content of said plasticizer being 65 to 80% by weight based on said ion sensitive membrane.

13. The ion sensor according to claim 2 or 6, wherein a particle diameter of said silver halide and of said silver in said modified silver halide layer is at most 1 $\mu$m.

14. The ion sensor plate according to claim 3, 4, 7 or 8, wherein said electric potential-stabilizing agent is silver halide.

15. The ion sensor plate according to claim 3, 4, 7, or 8, wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an ion sensitive material which is higher than that is required for responding to said specific ion.

16. The ion sensor plate according to claim 3, 4, 7 or 8, wherein said ion sensitive membrane contains an anion scavenger which is capable of protecting said ion sensitive membrane from being disturbed by an anion originating from said test liquid and/or said reference liquid, and said ion sensitive membrane contains a sufficient concentration of an electric potential-stabilizing agent which is higher than that is required for eliminating said disturbance by said anion.

17. The ion sensor plate according to claim 3, 4, 7 or 8, wherein said ion sensitive membrane contains at least a matrix, a plasticizer for plasticizing said matrix and an ion sensitive material, the content of said plasticizer being 65 to 80% by weight based on said ion sensitive membrane.

18. The ion sensor plate according to claim 4 or 8, wherein a particle diameter of said silver halide and of said silver in said modified silver halide layer is at most 1 $\mu$m.

* * * * *